(12) United States Patent
Kim et al.

(10) Patent No.: US 7,473,430 B2
(45) Date of Patent: Jan. 6, 2009

(54) CANCER CELL TARGETING GENE DELIVERY METHOD

(75) Inventors: Yeon-Soo Kim, Seoul (KR); In Seop So, Daejeon (KR); Young-Kwan Lee, Daejeon (KR); Jongpil Kim, Daejeon (KR); Moonkyung Kang, Daejeon (KR); Hyojeong Hong, Daejeon (KR)

(73) Assignee: Inje University (KR)

( * ) Notice: Subject to any disclaimer, the term of this patent is extended or adjusted under 35 U.S.C. 154(b) by 252 days.

(21) Appl. No.: 10/578,839

(22) PCT Filed: Mar. 15, 2004

(86) PCT No.: PCT/KR2004/000545

§ 371 (c)(1),
(2), (4) Date: May 10, 2006

(87) PCT Pub. No.: WO2005/047338

PCT Pub. Date: May 26, 2005

(65) Prior Publication Data

US 2007/0244032 A1    Oct. 18, 2007

(30) Foreign Application Priority Data

Nov. 12, 2003    (KR) .................. 10-2003-0079897

(51) Int. Cl.
*A61K 35/12* (2006.01)
*C12Q 1/68* (2006.01)
(52) U.S. Cl. ........................ 424/277.1; 435/6
(58) Field of Classification Search .............. None
See application file for complete search history.

(56) References Cited

U.S. PATENT DOCUMENTS 6,033,905 A    3/2000   Eiden et al.

OTHER PUBLICATIONS

Sausville et al. (2006) Cancer Res. 66(7): 3351-4.*
Johnson et al (2001) British Journal of Cancer. 84(10): 1424-1431.*
Fielding et al (2000) Human Gene Therapy. 11: 817-826.*
Goel et al (2000) Cancer Research. 60: 6964-6971.*
Marin, M., et al., "Targeted Infection of Human Cells via Major Histocompatibility Complex Class I Molecules by Moloney Murine Leukemia Virus-Derived Viruses Displaying Single-Chain Antibody Fragment-Envelope Fusion Proteins," J. of Virology, vol. 70, No. 5, May 1996, pp. 2957-2962.
Larson, S.M., et al., "Single Chain Antigen Binding Protein (sFv CC49): First Human Studies in Colorectal Carcinoma Metastatic to Liver," Supplement to Cancer, 1997, vol. 80, pp. 2458-2468.
Tang, Y., et al., "Tumor cell-specific gene transfer with retroviral vectors displaying single-chain antibody," Chinese Medical Journal, vol. 115, No. 7, 2002, pp. 1064-1069.

* cited by examiner

*Primary Examiner*—Bruce Campell
*Assistant Examiner*—Michelle Horning
(74) *Attorney, Agent, or Firm*—Sughrue Mion, PLLC

(57) ABSTRACT

The inventive chimeric ligand in the form of a fusion polypeptide of a single-chain antibody specific for Tag-72 surface antigen and GaLV envelope glycoprotein shows high transduction efficiency to cancer cells, specifically infects target cells and efficiently delivers a therapeutic gene. Accordingly, the inventive chimeric ligand can be effectively used for gene therapy to inhibit tumor growth and metastasis.

8 Claims, 13 Drawing Sheets

Fig. 4

HCMV Promoter

1     GALV ENV    685 AA
2     pHEFvGEL199   956 AA

MCMV Promoter

1     GALV ENV    685 AA
2     pMEFvGEL199   956 AA

Tag-72 (+)

LS174T     MCF-7

Anti-Tag72

Mock

Tag-72 (-)

MDA-B435    MDA-MB231    WIDR

Anti-Tag72

Mock

GP293/ScFv-GaLV Env expression packaging cells

GP293/Wild-type GaLV Env expression packaging cells

X 100

GP293/ScFv-GaLV Env expression packaging cells

GP293/Wild-type GaLV Env expression packaging cells

CANCER CELL TARGETING GENE DELIVERY METHOD

This is a National Stage application under 35 U.S.C. § 371 of PCT/KR2004/000545 filed on Mar. 15, 2004, which claims priority from Korean Patent Application 10-2003-0079897 filed Nov. 12, 2003, all of which are incorporated herein by reference.

FIELD OF THE INVENTION

The present invention relates to a chimeric ligand in the form of a fission polypeptide of a retrovirus envelope glycoprotein and a single chain antibody capable of specifically binding to a surface antigen of a tumor associated glycoprotein; an expression vector comprising a gene encoding said chimeric ligand; a packaging cell line transduced with said expression vector; a recombinant retrovirus produced by said packaging cell line; and a pharmaceutical composition comprising said chimeric ligand as an effective ingredient.

BACKGROUND OF THE INVENTION

Gene therapy is a rapidly emerging field that aims to treat acquired diseases such as cancer, diabetes and AIDS as well as inherent metabolic abnormality. Among several gene delivery vector systems currently used in gene therapy, the retrovirus vector system has advantages over others using adenovirus, liposome, electroporation and gene gun. For example, the retrovirus vector system has the ability to permanently integrate into host cells that allows stable expression of transduced cells. However, all of these systems have limitation in gene delivery to a specific target cell.

Several methods have been developed for specifically introducing a therapeutic gene into target cells using a retrovirus, e.g.; a method for linking a sugar molecule to an envelop glycoprotein of retrovirus by a chemical method so that the sugar-coupled envelope glycoprotein binds to an asialoglycoprotein receptor of target cells (Neda, H. et al., *J. Biol. Chem.* 266: 14143-14146, 1991); a method of using a coupling antibody bridge capable of binding to both of an envelop glycoprotein of retrovirus and a target cell's receptor or surface antigen (Goud, B. et al., *Virology* 163: 251-254, 1988; Roux, P. et al., *Proc. Natl. Acad. Sci. U.S.A.* 86: 9079-9083, 1989; Etienne-Julan, M. et al., *J. Gen. Virol.* 73: 3251-3255, 1992); a method for coupling a single-chain antibody to an envelope glycoprotein of retrovirus via genetic engineering and infecting target cells with the retrovirus (Russell, S. J. et al., *Nucleic Acids Res.* 21: 1081-1085, 1993; Somia, N. V. et al., *Proc. Natl. Acad. Sci. U.S.A.* 92: 7570-7574, 1995; Ager, S. et al., *Hum. Gene Ther.* 7: 2157-2164, 1996; Marin, M. et al., *J. Virol.* 70: 2957-2962, 1996; Schnierle, B. S. et al., *Gene Ther.* 3: 334-342, 1996); and a method for coupling a peptide ligand to the envelop glycoprotein of retrovirus via genetic engineering and infecting target cells with the retrovirus (Kasahara, N. et al., *Science* 266: 1373-1376, 1994; Cosset, F. L. et al., *J. Virol.* 69: 6314-6322, 1995; Schnierle, B. S., and Groner, B., *Gene Ther.* 3: 1069-1073, 1996). However, these methods show very low transduction efficiency.

There have also been developed methods using an avian or a murine retrovirus to introduce a therapeutic gene into human target cells (Chu, T-H. T., and R. Domburg, *J. Virol.* 69: 2659-2663, 1995; Chu, T-H. T. et al., *Gene Ther.* 1: 292-299, 1994; Valsesia-Wittmann, S. et al., *J. Virol.* 68: 4609-4619, 1994; Cosset, F-L. et al., *J. Virol.* 69: 6314-6322, 1995; Han, X. et al., *Proc. Natl. Acad. Sci. USA* 92: 9747-9751, 1995; Kasahara, N. et al., *Science* 266: 1373-1376, 1994; Somia, N. V., et al., *Proc. Natl. Acad. Sci. USA* 92: 7570-7574, 1995; HAN, J. Y., et al., *J. Virol.* 71, 8103-8108, 1997). The structure and function of a murine retrovirus have been widely studied, and, in particular, the tertiary structures of Mo-MuLV and Fr-MuLV envelope glycoproteins have been recently established by X-ray crystallography.

If the receptor or surface antigen of target cells is identified and specific, a method for coupling a single-chain antibody (ScFv) to an envelope glycoprotein of retrovirus via genetic engineering and infecting target cells with the retrovirus is very useful for the specific infection of target cells.

Single chain antibody (ScFv) is formed by joining the carboxy-terminal of $V_H$ and the amino-terminal of $V_L$ segments with a suitable synthetic amino acid linker. The antibody combining site is located at the Fv region of the molecule formed by the variable domains of heavy and light chains ($V_H$ and $V_L$) (Poon et al., *Molecular Immunology* 39: 19-24, 2002; Fujiwara et al., *Biochemistry* 41: 12729-12738, 2002).

Recently, the pseudotyping of retrovirus has been studied to improve stability and transduction efficiency. For example, a gibbon ape leukemia virus (GaLV) Env-pseudotype retroviral vector showed 5 to 30 times higher infection efficiency than an amphotropic murine retroviral vector in several human cell lines (Kim et al., *Proc. Amer. Assoc. Cancer Res.* 38: 177, 1997). However, the limitation in specific targeting is remained to be solved.

Therefore, the present inventors have endeavored to meet the need of a gene delivery system using a retrovirus which shows higher viral titer and transduction efficiency, and develop a chimeric ligand in the form of a fusion polypeptide of the GaLV envelope glycoprotein and a single chain antibody derived from monoclonal antibody capable of specifically binding to a surface antigen of tumor associated glycoprotein 72 (Tag-72).

SUMMARY OF THE INVENTION

Accordingly, it is an object of the present invention to provide a retroviral gene delivery system capable of specifically targeting cancer cell which is useful for anti-tumor gene therapy.

In accordance with one aspect of the present invention, there is provided a chimeric ligand in the form of a fusion polypeptide of a retrovirus envelope glycoprotein (Env GP) and a single chain antibody (ScFv) capable of specifically binding to a surface antigen of a tumor-associated glycoprotein 72 (Tag-72).

In accordance with another aspect of the present invention, there is provided a recombinant expression vector comprising a gene encoding said chimaric ligand and a packaging cell line capable of producing a retrovirus by transducing with said expression vector.

In accordance with another aspect of the present invention, there is provided a pharmaceutical composition for cancer cell targeting gene therapy which comprises said chimeric ligand or packaging cell line as an effective ingredient.

BRIEF DESCRIPTION OF THE DRAWINGS

The above and other objects and features of the present invention will become apparent from the following description of the invention, when taken -in conjunction with the accompanying drawings, which respectively show.

| | |
|---|---|
| a: signal peptidase cleavage site, | b: SU/TM cleavage site, |
| c: R-peptide cleavage site, | SP: signal peptide, |
| VRA: variable region A, | VRB: variable region B, |
| VRC: variable region C, | RBD: receptor binding domain, |
| PRR: proline rich region, | CT: C-terminal region of SU, |
| SU: surface subunit, | FP: fusion protein, |
| Anc: anchorage region, | RP: R-peptide, |
| TM: transmembrane domain | |

Figure 2:
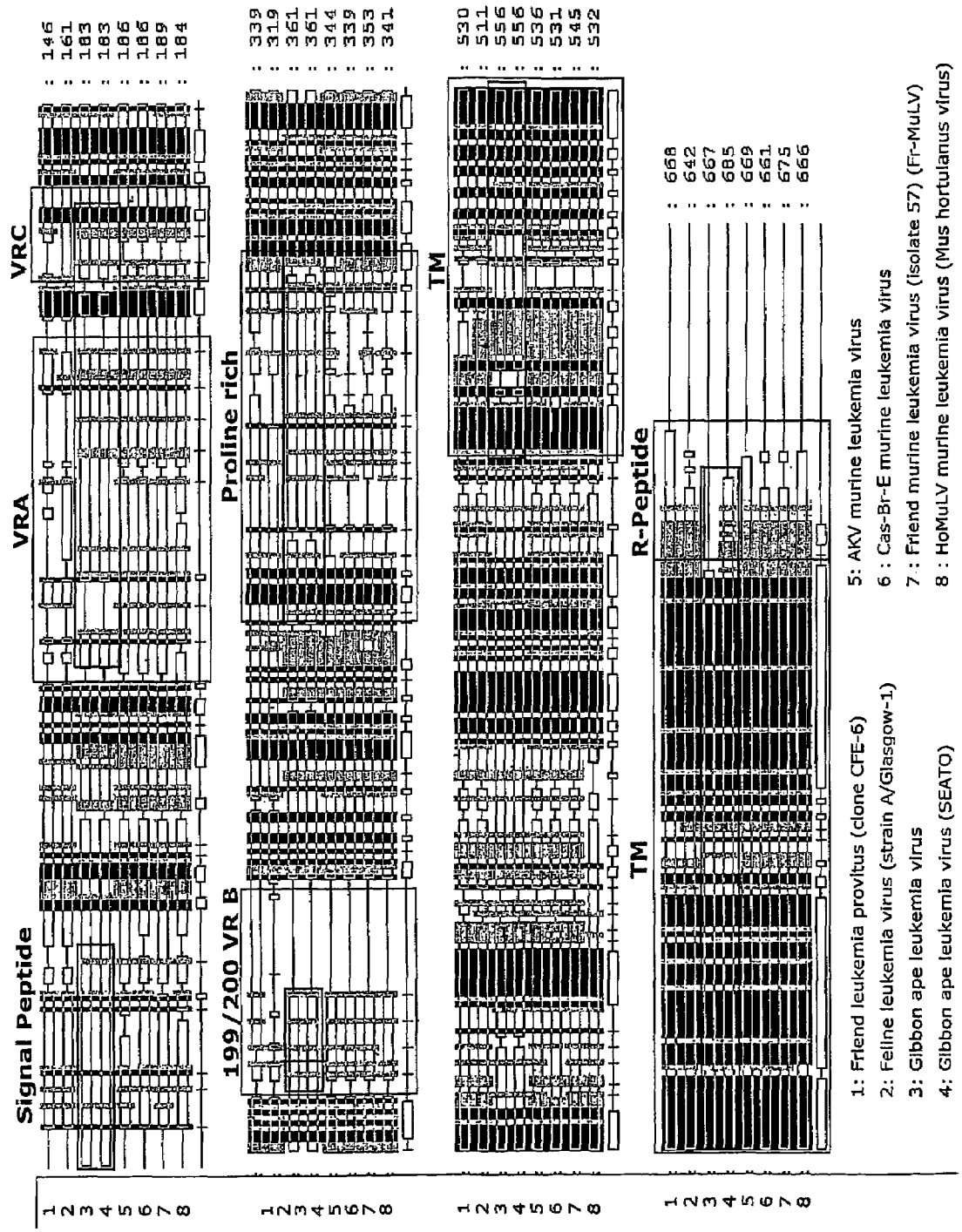

FIG. 2: the result of amino acid alignment analysis of several retrovirus envelope glycoproteins,

| | |
|---|---|
| VRA: variable region A, | VRB: variable region B, |
| VRC: variable region C, | PRR: proline rich region, |
| SU: surface subunit, | TM: transmembrane domain |

Figure 3:
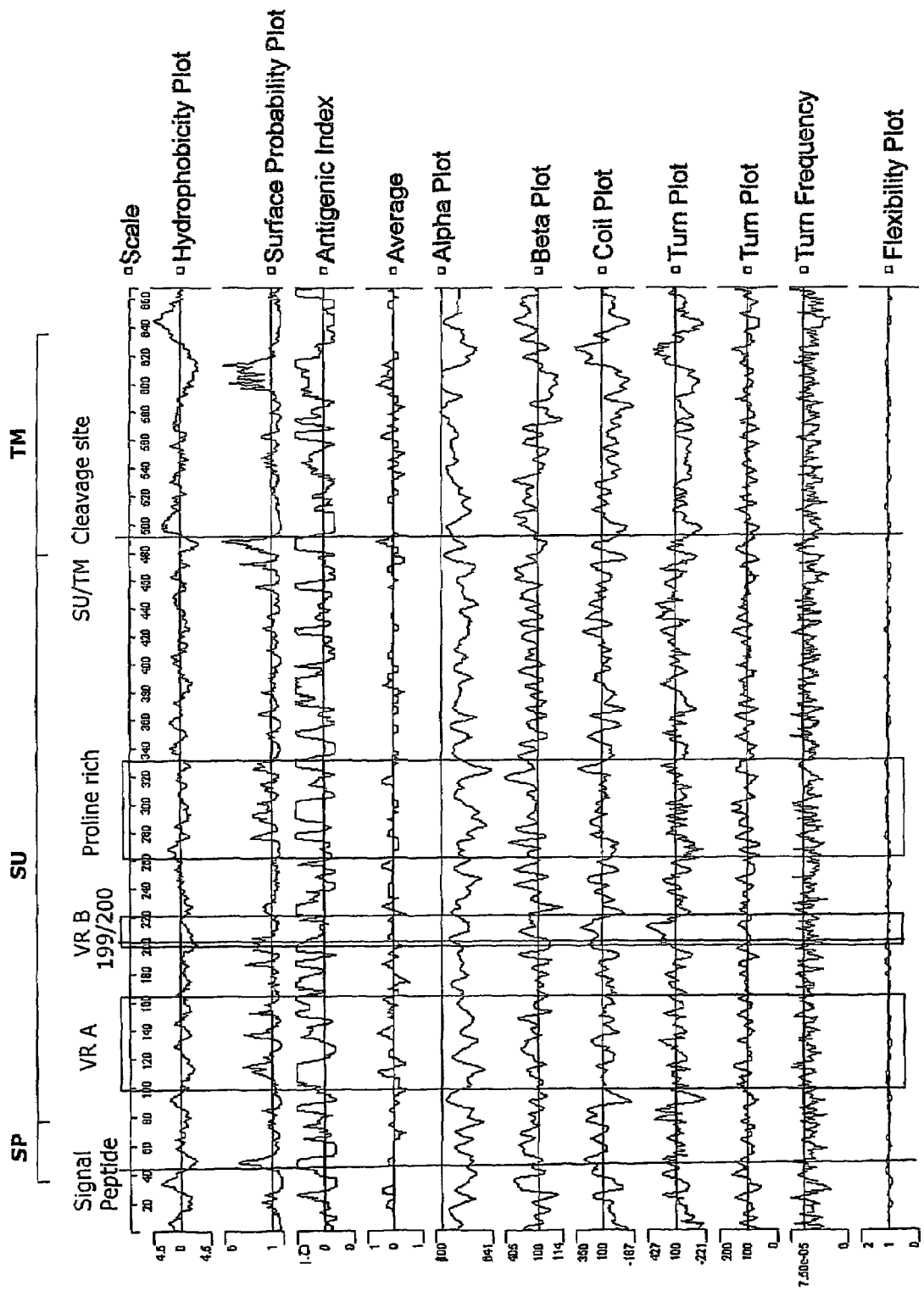

FIG. 3: the analysis of secondary structure of GaLV envelope glycoprotein,

| | |
|---|---|
| VRA: variable region A, | VRB: variable region B |
| SU: surface subunit, | TM: transmembrane domain |

Figure 5:
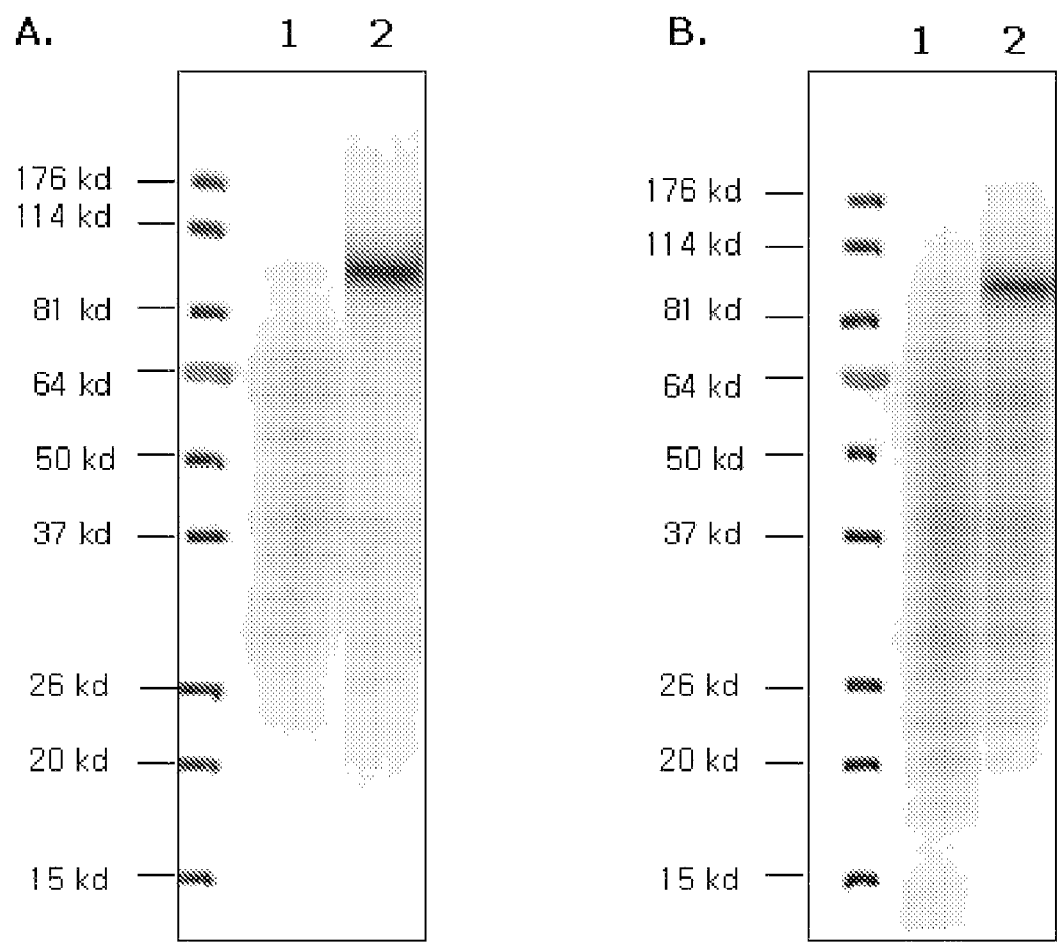

FIG. 4: the schematic illustration of vectors expressing the inventive ScFv-GaLV Env GP chimeric ligand FvGEL199 and wild type GaLV envelope glycoprotein, respectively, FIG. 5: the photographic illustrations of western blot analyses examining the expression of chimeric ligand FvGEL199 in a packaging cell line, A: FvGEL199 expressed in a vector whose expression is regulated by HCMV promoter, Lane 1: GP293 cell extract comprising pHEGEL, Lane 2: GP293 cell extract comprising pHEFvGEL199, FIG. 6: the photographic illustrations of western blot analysis examining the production of a recombinant retrovirus containing the ScFv-GaLV Env GP chimeric ligand FvGEL199, Lane 1: viral pellets obtained from cell culture media of GP293 comprising pHEGEL, Lane 2: viral pellets obtained from cell culture media of GP293 comprising pHEFvGEL199, FIGS. 7a and 7b: the photographic illustrations of FACS and immunohistochemical analyses examining the expression of Tag-72 surface antigen in several human cancer cell lines, FIG. 8: the photographic illustration of transduced cells with recombinant retrovirus comprising pHEFvGEL199, FIG. 9: the photographic illustrations of transduced cells with lacZ expression recombinant retrovirus obtained by transducing the inventive packaging cell lines GP293HEFvGEL199 and GP293HEGEL with lacZ expression retrovirus vector, respectively, FIG. 10: the photographic illustrations of transduced cells with lacZ expression recombinant retrovirus obtained from the stably estabilished, inventive virus producing cell lines GP293HEFvGEL199/lacZ and GP293HEGEL/lacZ respectively, FIG. 11a: dissecting microscope pictures (×10) observed when Tag-72 positive or negative cell line was intravenously injected, respectively, FIG. 11b: a graph showing the number of nodules observed in FIG. 11a, FIG. 12a: dissecting microscope pictures showing the in vivo transduction of LacZ gene by the inventive ScFv-GaLV Env GP chimeric ligand FvGEL199 expression retrovirus, and FIG. 12b: a graph showing the relative in vivo transduction efficiency of LacZ gene observed in FIG. 12a.

DETAILED DESCRIPTION OF THE INVENTION

The present invention provides a chimeric ligand in the form of a fusion polypeptide of GaLV envelope glycoprotein and a single chain antibody specific for the surface antigen of tumor-associated glycoprotein 72 (Tag-72).

In order to develop a retrovirus gene delivery system, the present inventors have employed a single chain antibody which is capable of specifically binding to the surface antigen of tumor-associated glycoprotein 72 (Tag-72) expressed in various cancer cells including colon, stomach, breast, ovary and prostate cancers. Further, in order to efficiently introduce a therapeutic gene into human target cells, the present inventors have employed GaLV (gibbon ape leukemia virus) envelope glycoprotein which shows higher transduction efficiency into human cancer cells and more stable in human blood than MuLV (Murine Leukemia Virus) envelope glycoprotein.

The binding of envelope glycoproteins distributed on a viral envelope to cell receptors on a cell surface is essential for the infection of retrovirus into target cells, which is the key to determine the specificity of infectiousness. In a target cell specific gene delivery system, it is possible to produce a virus capable of specifically infecting target cells by manipulating a viral envelope glycoprotein endowing a cell specificity to bind to be coupled to a receptor of a target cell. Therefore, the present inventors have prepared a chimeric ligand by fusing single chain antibody Tag-72pS 1 specific for Tag-72 surface antigen to a surface subunit (SU) region which determines the cell specificity of GaLV envelope glycoprotein and is capable of binding to a specific cell receptor. A retrovirus expressing the envelope glycoprotein fused with the single-chain antibody is capable of specifically binding to target cells and effectively delivering a therapeutic gene thereto.

In case of MuLV envelope glycoprotein having a structure similar to GaLV envelope glycoprotein, it has been reported that point mutation, insertion mutation or deletion mutation introduced into the envelope glycoprotein may lead to a conformational change, to produce a viral envelope glycoprotein having an abnormal function, and therefore, the viral infectiousness deteriorates (Russell, S. J. et al., *Nucleic Acids Res.* 21: 1081-1085, 1993; Somia, N. V. et al., *Proc. Natl. Acad. Sci. U.S.A.* 92: 7570-7574, 1995; Ager, S. et al., *Hum. Gene Ther.* 7: 2157-2164, 1996; Marin, M. et al., *J. virol.* 70: 2957-2962, 1996; Schnierle, B. S. et al., *Gene Ther.* 3: 334-342, 1996; Chris A. Benedict. et al., *Human Gene Therapy* 10: 545-557, 1999; Mariana Marin. et al., *Journal of Virology* 70: 2957-2962, 1996; Te-Hua Tearina C. H. and Ralph Dornburg, *Journal of Virology* 71: 720-725, 1997). Namely, when a foreign peptide is inserted into an envelope glycoprotein, or a certain portion of an envelope glycoprotein is deleted, virus having a significantly reduced infectiousness is produced. Accordingly, when a foreign ligand such as ScFv is inserted into a retrovirus envelope glycoprotein, the relationship between the envelope glycoprotein's structure and function must be carefully evaluated. The inventive chimeric ligand is so designed as to specifically infect target cells by inserting a single-chain antibody (ScFv) into a variable region B (VRB) selected among several SU regions of envelope glycoprotein which determine the cell specificity and cell surface binding.

In a preferred embodiment, the present inventors have prepared a fusion chimeric ligand which is prepared by inserting single-chain antibody Tag-72pS1 specifically binding to Tag-72 surface antigen into a site between the 199$^{th}$ and 200$^{th}$ amino acid residues starting from the first methionine translated from ATG initiation codon which is a variable region B of GaLV envelope glycoprotein; and an expression vector comprising said chimeric ligand. The GaLV envelope glycoprotein used in the present invention is a SEATO type having an R-peptide and has the nucleotide sequence of SEQ ID NO: 7 (NCBI Accession No. AAC96083). Further, the single-chain antibody Tag-72pS1 specific for the Tag-72 surface antigen has the nucleotide sequence of SEQ ID NO: 8. The inventive chimeric ligand designated FvGEL199 has the nucleotide sequence of SEQ ID NO: 10 and encodes a fusion polypeptide having the amino acid sequence of SEQ ID NO: 11, wherein the single-chain antibody Tag-72pS1 is coupled to the GaLV envelope glycoprotein by a linker comprising 5 amino acids of Gly$_4$Ser.

The single-chain antibody GaLV envelope glycoprotein (ScFv-GaLV Env GP) chimeric ligand thus prepared is cloned in backbone vector pHYKEF1 (Kim et al., *J. Biotechnol.* 93: 183, 2002) whose expression is regulated by HCMV promoter and the transcription activity is stimulated by EF1a intron, to obtain expression vectors pHEFvGEL199. The resulting expression vectors express the fusion polypeptide comprising 956 amino acids formed by inserting the single-chain antibody Tag-72pS1 into the site between the 199$^{th}$ and 200$^{th}$ amino acid residues of GaLV envelope glycoprotein SU region.

In a preferred embodiment of the present invention, *E. coli* DH5α was transformed with expression vector pHEFv-GEL199 and to obtain *E. coli* transformants designated DH5α/pHEFvGEL199, which were deposited on Feb. 13, 2004 with the Korean Collection for Type Cultures (KCTC) (Address: Korea Research Institute of Bioscience and Biotechnology (KRIBB), #52, Oun-dong, Yusong-ku, Taejon, 305-333, Republic of Korea) under the accession numbers KCTC-10596BP, in accordance with the terms of Budapest Treaty on the International Recognition of the Deposit of Microorganism for the Purpose of Patent Procedure.

The present invention also provides a packaging cell line producing a retrovirus which is transduced with a recombinant retroviral vector comprising a gene encoding the inventive chimeric ligand.

It is preferable that the cell line employable in the present invention is a packaging cell line which can express Gag-Pol proteins but does not contain any viral envelope glycoprotein capable of mediating virus infection into animal cell lines, for example, GP293 cell line (Clontech). Preferably, the method for transducing a retrovirus is performed by employing any one of conventional methods well-known in the art such as a calcium phosphate coprecipitation method (Sambrook et al., *Molecular Cloning* 2nd ed., 1989) and a lipofectamin method (Invitrogen, USA). Transduced cell lines may be selected as a colony by culturing them in an appropriate selection medium containing antibiotics such as G418. In a preferred embodiment of the present invention, packaging cell line GP293 cells have been transduced with the recombinant retroviral vector pHEFvGEL199, and then, packaging cell line GP293HFvGEL199 capable of producing a recombinant retrovirus at a high viral titer is selected from the transduced cell lines.

The packaging cell line thus selected can be effectively introduced into human cancer cells in a target cell specific manner and efficiently express the chimeric ligand, which effectively inhibits cancer cells from growing and metastasizing.

Accordingly, the present invention further provides a pharmaceutical composition comprising an effective dose of the inventive packaging cell line or the inventive chimeric ligand and a pharmaceutically acceptable carrier.

The inventive pharmaceutical formulation may be prepared in accordance with any one of the conventional procedures. In preparing the formulation, the effective ingredient is preferably admixed or diluted with a carrier. Examples of suitable carriers, excipients, or diluents are lactose, dextrose, sucrose, sorbitol, mannitol, starches, gum acacia, alginates, gelatin, calcium phosphate, calcium silicate, cellulose, methylcellulose, microcrystalline cellulose, polyvinylpyrrolidone, water, methylhydroxybenzoates, propylhydroxybenzoates, talc, magnesium stearate and mineral oil. The formulation may additionally include fillers, anti-agglutinating agents, lubricating agents, wetting agents, flavoring agents, emulsifiers, preservatives and the like. The composition of the invention may be formulated so as to provide a quick, sustained or delayed release of the active ingredient after it is administrated to a patient, by employing any one of the procedures well known in the art.

The pharmaceutical formulation of the present invention can be administered via intramuscular injection. Preferably, the inventive formulation is an isotonic solution or a suspension.

For treating a human patient, a typical daily dose of the inventive packaging cell line as an effective ingredient may range from about 10$^5$ to 10$^8$ cells/kg body weight, preferably 10$^6$ to 10$^7$ cells/kg body weight, and can be administered in a single dose or in divided doses. However, it should be understood that the amount of the active ingredient actually administered ought to be determined in light of various relevant factors including the condition to be treated, the chosen route of administration, the age, sex and body weight of the individual patient, and the severity of the patient's symptom; and, therefore, the above dose should not be intended to limit the scope of the invention in any way.

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usage and conditions.

EXAMPLE 1

Preparation of a Recombinant Retroviral Vector Expressing ScFv-GaLV Envelope Glycoprotein Chimeric Ligand <1-1> Structural and Functional Analyses of GaLV Envelope Glycoprotein A chimeric ligand was prepared in the form of a fusion polypeptide of single-chain antibody Tag-72pS1 specific for Tag-72 surface antigen and GaLV envelope glycoprotein (Env GP) as follows.

Figure 1:
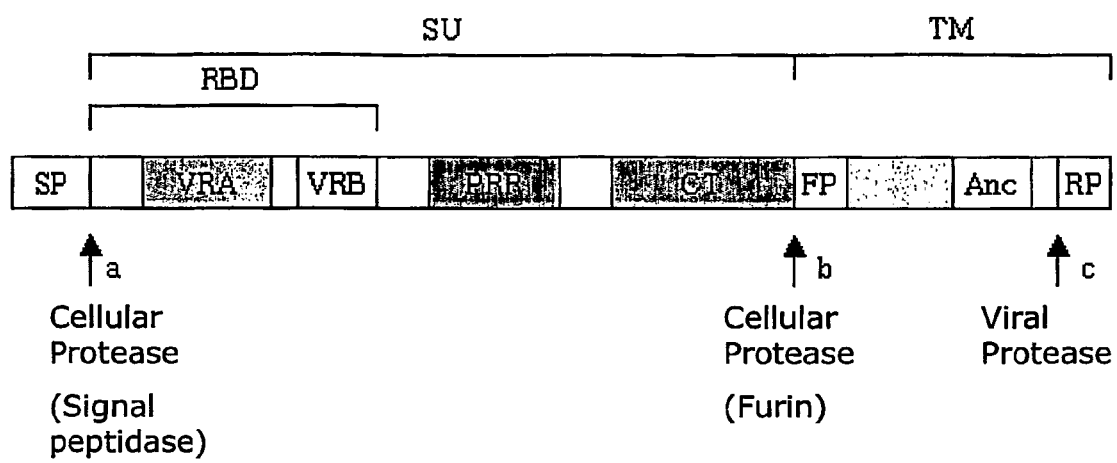
FIG. 1: the structure of an envelope glycoprotein of mammalian type-C retrovirus similar to a GaLV envelope glycoprotein (GaLV Env GP)

Unlike the envelope glycoproteins of other retroviruses such as MuLV and HIV or a haemagglutinin (HA) of influenza A virus, no information was available about the three dimensional structure and function of GaLV envelope glycoprotein. Accordingly, the structural and functional relationship analyses between GaLV envelope glycoprotein and other retrovirus envelope glycoproteins were carried out to select a proper site of the GaLV envelope glycoprotein where the single-chain antibody is to be inserted. The present inventors carried out a homology search between the GaLV envelope glycoprotein and other retrovirus envelope glycoproteins using Pfarm analysis (Protein Families Database of Alignments and HMMs). As a result, it was found that some of these retrovirus envelope glycoproteins have a characteristic surface subunit (SU) structure unique for the GaLV envelope glycopeotein which comprises a variable region A (VRA), variable region B (VRB), variable region C (VRC) and proline rich region (PRR), as well as an R-peptide at a carboxyl terminal (C-terminal) of transmembrane domain (TM). Further, the sequence homology between envelope glycoproteins of mammalian type-C retrovirus Fr-MuLV, gamma retrovirus GaLV, FLV and MuLV were examined using several computer programs. As a result, it was discovered that except for the receptor binding domain (RBD) known as a specific receptor binding site, the proline rich region (PRR) having an unknown function and C-terminal region, they showed high sequence homology and identity (Table 1 and FIG. 1).

secondary structure of GaLV Env glycoprotein was compared with the secondary structure of Fr-MuLV glycoprotein to predict a suitable insertion site of a hypothetical tertiary structure of GaLV Env glycoprotein as a counter part of the known tertiary structure of FrMuLV Env glycoprotein. Form these results, a variable region B (VRB) was selected as a suitable site for the insertion of a single-chain antibody specific for Tag-72 surface antigen, the VRB being a receptor binding domain (RBD) involved in a specific recognition and binding of GaLV envelope glycoprotein to a target cell receptor.

FIG. 3 shows the secondary structures of retrovirus envelope glycoproteins, the insertion site of the single-chain antibody glycoprotein into GaLV envelope glycoprotein being represented by a red solid line between the $199^{th}$ and $200^{th}$ amino acid residues of variable region B, the position in the amino acid sequence being identified by numbers, and the amino acid sequence thus numbered containing a signal peptide having methionine as the $1^{st}$ amino acid.

<1-2> Preparation of a Fusion Chimeric Ligand of Single-chain Antibody and Retrovirus Envelope Glycoprotein A chimeric ligand in the form of a fusion polypeptide of GaLV envelope glycoprotein and single-chain antibody Tag-

TABLE 1

| Envelope glycoprotein | NCBI Accession NO | Virus | Retrovirus type | Homology (%) | Identity (%) |
|---|---|---|---|---|---|
| Env_GaLV/1-685 | AAC96083 | Gibbon ape leukemia virus (SEATO) | Gamma | 100 | 100 |
| Env_GaLV/1-667 | AAA46811 | Gibbon ape leukemia virus | Gamma | 97 | 97 |
| Env_FLVC6/1-668 | AAA30809 | Friend leukemia provirus (clone CEF-6) | Gamma | 61 | 39 |
| Env_FLVGL/1-642 | AAA43053 | Feline leukemia virus (strain A/Gasgow-1) | Gamma | 63 | 41 |
| Env_MLVF5/1-675 | CAA26561 | Friend murine leukemia virus (isolate 57) (Fr-MuLV) | Mammalian C | 66 | 46 |
| Env_MLVCB/1-661 | AAA46512 | Cas-Br-E murine leukemia virus | Gamma | 65 | 45 |
| Env_MLVHO/1-666 | M26527 | HoMuLV murine leukemia virus (*Mus hortulanus* virus) | Gamma | 64 | 43 |
| Env_MLVAV/1-669 | AAB03092 | AKV murine leukemia virus | Gamma | 64 | 45 |

Examined based on the results of the sequence homology analyses was a suitable site of GaLV envelope glycoprotein for inserting a single-chain antibody specific for Tag-72 surface antigen by analyzing the secondary structure of GaLV envelope glycoprotein in relation with the known tertiary structure of Fr-MuLV envelope glycoprotein (NCBI PDB Accession NO: 1AOL). Since the conserved region of an amino acid sequence is regarded as a structurally and functionally important region from an evolutional point of view, attention was paid first to the highly variable region which has flexibility in the course of mutation, natural selection, adaptation or evolution. Therefore, a highly variable region of GaLV envelope glycoprotein was examined based on amino acid alignment analysis of several subtypes of GaLV envelope glycoproteins and various mammalian type-C retrovirus envelope glycoproteins (FIG. 2). Next, to determine a suitable site that minimizes the structural and functional change of the envelope glycoprotein, secondary structural analysis of GaLV Env glycoprotein was conducted in terms of hydropathy, surface probability, antigenic index, α-helix, β-sheet, coil structure, turn plot, turn frequency and flexibility. Further, the 72pS1 specific for Tag-72 surface antigen was prepared from heavy- and light-chain variable regions of AKA humanized antibody (KOREA Patent NO: 318761) using the method disclosed by Huston et al (Huston et al., *Proc. Natl. Acad. Sci. U.S.A.* 85: 5879-5883, 1988). The single-chain antibody thus prepared was inserted into the SfiI/NotI restriction sites of pCANTAB5E vector to obtain vector pCANTAB-3E8ScFvPreS1. A wild-type GaLV envelope glycoprotein gene (SEATO) (NCBI Accession No. AAC96083) was inserted into vector pHYKEF-1 (Kim et al., *J. Biotechnol.* 93: 183, 2002) to obtain vector pHEGEL. pCANTAB-3E8ScFvPreS1 and pHEGEL vectors thus prepared were subjected to PCR amplification to prepare a chimeric ligand.

The GaLV envelope glycoprotein gene cloned in vector pHEGEL was a SEATO type having an R-peptide and has the nucleotide sequence of SEQ ID NO: 7. The gene encoding the single-chain antibody Tag-72pS1 specific for Tag-72 surface antigen inserted in pCANTAB-3E8ScFvPreS1 vector has the nucleotide sequence of SEQ ID NO: 8, wherein the single-chain antibody Tag-72pS1 is expressed in the form of a single chain containing the carboxy terminal of the heavy chain (H)

variable region $V_H$ coupled to the amino terminal of the light chain (L) variable region $V_L$ through a linker comprising 15 amino acids of $(Gly_4Ser)_3$. A PreS1 epitope of SEQ ID NO: 9 was tagged to the C-terminal of the single-chain antibody. To prepare the chimeric ligand formed by inserting the single-chain antibody Tag-72pS1 at between the 199th and 200th amino acid residues starting from the first methionine, PCR was performed as follows.

Vector pHEGEL was subjected to PCR using Env F primer of SEQ ID NO: 1 and 597LN primer of SEQ ID NO: 2 to amplify 680 bp PCR product. Vector pHEGEL was subjected to PCR using LC597 primer of SEQ ID NO: 3 and Spike R2 primer of SEQ ID NO: 4 to amplify 1,500 bp PCR product. Vector pCANTAB-3E8ScFvPreS1 was subjected to PCR using LnkNScFv primer of SEQ ID NO: 5 and ScFvLnkC primer of SEQ ID NO: 6 to amplify 820 bp PCR product. Three PCR products thus obtained were all mixed together, and subjected to PCR using Env F primer of SEQ ID NO: 1 and Spike R2 primer of SEQ ID NO: 4 to amplify 2,930 bp PCR product. The PCR reaction solution was prepared by mixing 200 ng of template DNA, 5 units of polyinerase, 10 µl of PCR buffer solution, 0.2 mM of dNTP and 50 pmole each of primers and adjusted to a final volume of 100 µl. The PCR buffer solution comprised 200 mM Tris-HCl, 100 mM KCl, 100 mM $(NH_4)_2SO_4$, 20 mM $MgSO_4$, 1% triton X-100 and 1 mg/ml acetylated BSA (pH 8.8). The polymerase employable in the present invention was Pfu DNA polymerase (Bioneer, KOREA) or Takara Ex Taq polymerase (TaKaRa, JAPAN). The PCR condition consisted of an initial denaturation reaction for 4 min at 94° C.; 30 cycles of amplification reaction for 1 min at 94° C. (denaturation), 1 min at 55° C. (annealing) and 3 min at 72° C. (extension); and an final amplification for 10 min at 72° C.

The 2,930 bp PCR product encoding the ScFv-GaLV envelope glycoprotein chimeric ligand gene thus obtained was digested with restriction enzymes BamHI and XbaI. The fragment was inserted into the same restriction enzyme sites of highly efficient gene expression vector pHYKEF1 to obtain recombinant vectors pHEFvGEL199-expressing the ScFv-GaLV envelope glycoprotein chimeric ligand gene, wherein the expression of the foreign gene in vector pHYKEF1 and was regulated by HCMV promoter, and its transcription was activated by EF1α intron (Kim et al., *J. Biotechnol.* 93: 183, 2002). As a control, the wild-type GaLV (SEATO) envelope glycoprotein gene was inserted into the above backbone vector to obtain expression vector pHEGEL. From the results of nucleotide sequence analysis, it was confirmed that the inventive chimeric ligand gene was inserted into each of the expression vector pHEFvGEL199. The ScFv-GaLV envelope glycoprotein chimeric ligand was designated FvGEL199.

The inventive chimeric ligand thus prepared had the nucleotide sequence of SEQ ID NO: 10 which encodes the fusion polypeptide having the amino acid sequence of SEQ ID NO: 11. FIG. 4 represents a schematic diagram of the ScFv-GaLV envelope glycoprotein fusion chimeric ligand FvGEL199. The retroviral vector pHEGEL expressed the wild-type GaLV envelope glycoprotein consisting of 685 amino acids. Further, the recombinant retroviral vector pHEFvGEL199 expressed the fusion polypeptide consisting of 956 amino acids formed by inserting the single-chain antibody Tag-72pS1 at between the 199th and the 200th amino acid residues in the SU region of GaLV envelope glycoprotein. The single-chain antibody Tag-72pS1 in the inventive fusion chimeric ligand was coupled to the GaLV envelope glycoprotein by a linker comprising 5 amino acids of $Gly_4Ser$.

<1-3> Expression of ScFv-GaLV Env GP Chimeric Ligand

In order to produce a retrovirus expressing the inventive ScFv-GaLV Env glycoprotein chimeric ligand, it has to be expressed in the form of the chimeric ligand in host cells; the expressed chimeric ligand is subjected to posttranslational modification, trimerization and SU/TM digestion in golgi apparatus; transferred to a cell surface, and then, distributed on a viral envelope membrane during viral packaging. The chimeric ligand distributed on the viral envelope would then recognize and bind to a specific receptor of target cells during viral infection to penetrate into the cell interior, and then, the viral particle is taken up into the cytoplasm via inter-membrane fusion. Thus, it was examined whether the recombinant retroviral vector pHEFvGEL199 prepared in Example <1-2> would express the inventive ScFv-GaLV Env glycoprotein chimeric ligand, as follows.

Human kidney epithelial cells such as 293 or 293T cells were distributed on a 6-well plate at a concentration of $2 \times 10^5$ cells/well one day before transfection, and subjected to transfection with the recombinant retroviral vector pHEFvGEL199, respectively, using LIPOFECTAMIN PLUS® (a transfection reagent) (Invitrogen, USA) according to the manufacture's instruction. At this time, cells transduced with pHEGEL vector were employed as a control which do not express the chimeric ligand. The transduced cells were cultured in DMEM (Dulbecco's modified Eagle's medium, Gibco BRL) supplemented with 10% fetal bovine serum (FBS, HyClone), 100 U/ml of penicillin G and 0.1 mg/ml streptomycin at 37° C. for 3 to 6 hrs. After the cells were transferred into a fresh medium and further cultured for 2 days, the cultured cells were harvested and subjected to centrifugation to isolate cell pellets. The cell pellets were suspended in 100 µl of phosphate buffer solution (PBS) and an equal volume of SDS-PAGE sample buffer solution (4% SDS, 20% glycerol, 10% β-mercaptoethanol, 0.05% bromo phenol blue, 125 mM Tris-HCl, pH 6.8) was added to the cell suspension. The sample was subjected to electrophoresis, and western blot analysis was conducted to examine the expression of fusion chimeric ligand.

SDS-PAGE was carried out according to the method of Laemmli (Laemmli, U. K., *Nature* 277: 680-685, 1970). The fusion chimeric ligand developed on the electrophoresis gel was transferred to a PVDF membrane using a transfer buffer solution (10 mM glycine, 20% methanol, 0.1% SDS, 100 mM Tris-HCl) under an electric current of 80 V for 3 hrs. Western blot analysis was carried out according to the method of Towbin (Towbin, H. et al., *Proc. Natl. Acad. Sdi. USA* 76: 4350-4354, 1979). The membrane blot was washed with a TBST buffer solution (150 mM NaCl, 0.1% tween 20,20 mM Tris-HCl, pH 7.4) for 5 min and soaked in the TBST buffer solution supplemented with 5% (w/v) non-fat milk powder (TTM-5%) at 4° C. overnight. A mouse monoclonal antibody raised against the PreS 1 epitope (Aprogen, KOREA) of SEQ ID NO: 9 tagged at the C-terminal of ScFv was employed as a primary antibody to confirm the expression of ScFv-GaLV Env glycoprotein fusion chimeric ligand FvGEL199. The primary antibody was diluted with a TTM-5% buffer solution in a ratio ranging from 1: 1,000 to 1: 4,000, and reacted with the PVDF membrane at room temperature for 3 hrs. The membrane was washed three times with a TTM-0.5% buffer solution at an interval of 10 min, and reacted with a secondary antibody at room temperature for 3 hrs, the secondary antibody being prepared by diluting HRP-conjugated goat anti-body anti mouse IgG with a TTM-0.5% buffer solution in a ratio ranging from 1: 1,000 to 1: 2,000. After the reaction was completed, the membrane was washed five times with a TTM-0.5% buffer solution at an interval of 10 min, and then, washed with a TBS buffer solution (150 mM NaCl, 20 mM Tris-HCl, pH 7.4) for 5 min. Immunoblot analysis was carried out using a chemiluminescence system (SantaCruz) and KODAK BIOMAX MR® film according to the manufacture's instruction. The molecular weight of protein was measured by using a prestained protein marker (Bio-Rad) during the electrophoration.

As a result, the inventive fusion chimeric ligand FvGEL199 showed a band caused by antigen-antibody immune reaction at a position corresponding to the molecular weight of a peptide comprising 718 amino acids after cleavage of signal peptide and TM regions being detected (Lane 2 of FIG. 5), but for pHEGEL vector, there was no band detected (Lane 1 of FIG. 5). From these results, it was found that the transduced cells with the respective inventive recombinant expression vector pHEFvGEL199 express the fusion chimeric ligand of ScFv-GaLV Env glycoprotein.

E. coli DH5α was transformed with expression vector pHEFvGEL199 and to obtain E. coli transformants designated DH5α pHEFvGEL199, which were deposited on Feb. 13, 2004 with the Korean Collection for Type Cultures (KCTC) (Address: Korea Research Institute of Bioscience and Biotechnology (KRIBB), #52, Oun-dong, Yusong-ku, Taejon, 305-333, Republic of Korea) under the accession numbers KCTC-10596BP, in accordance with the terms of Budapest Treaty on the International Recognition of the Deposit of Microorganism for the Purpose of Patent Procedure.

EXAMPLE 2

Transduction of Retrovirus Expressing the ScFv-GaLV Env GP Chimeric Ligand

<2-1> Preparation of Retrovirus Expressing the ScFv-GaLV Env GP Chimeric Ligand

Figure 6:
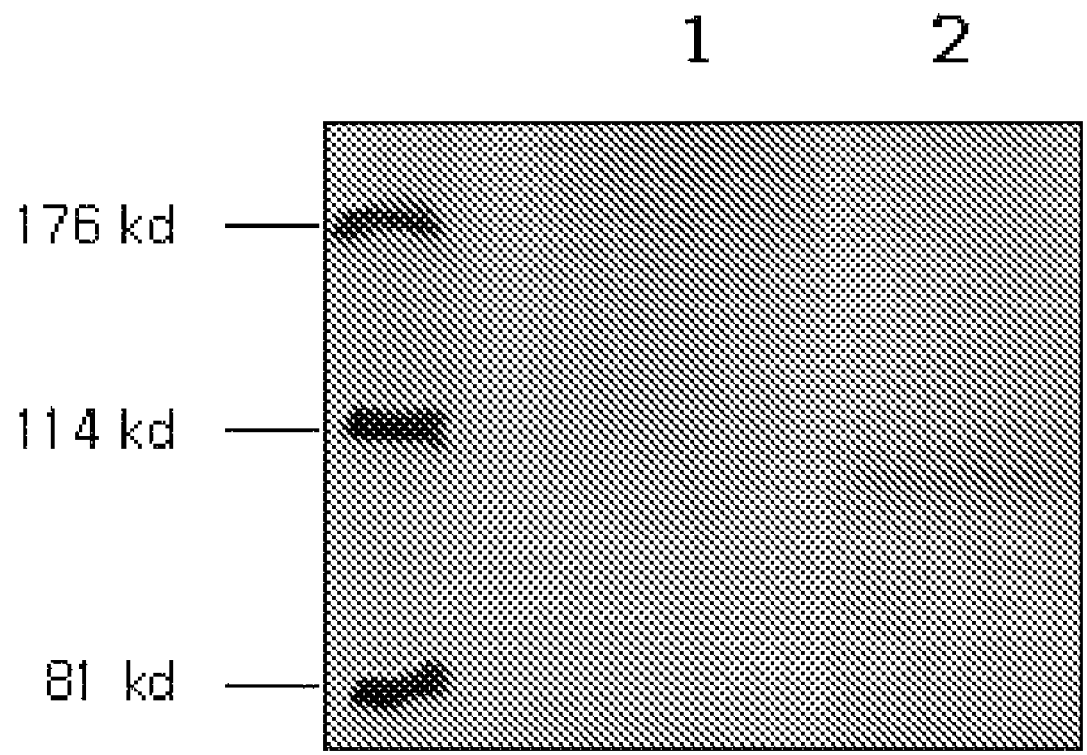
Figure 7A:
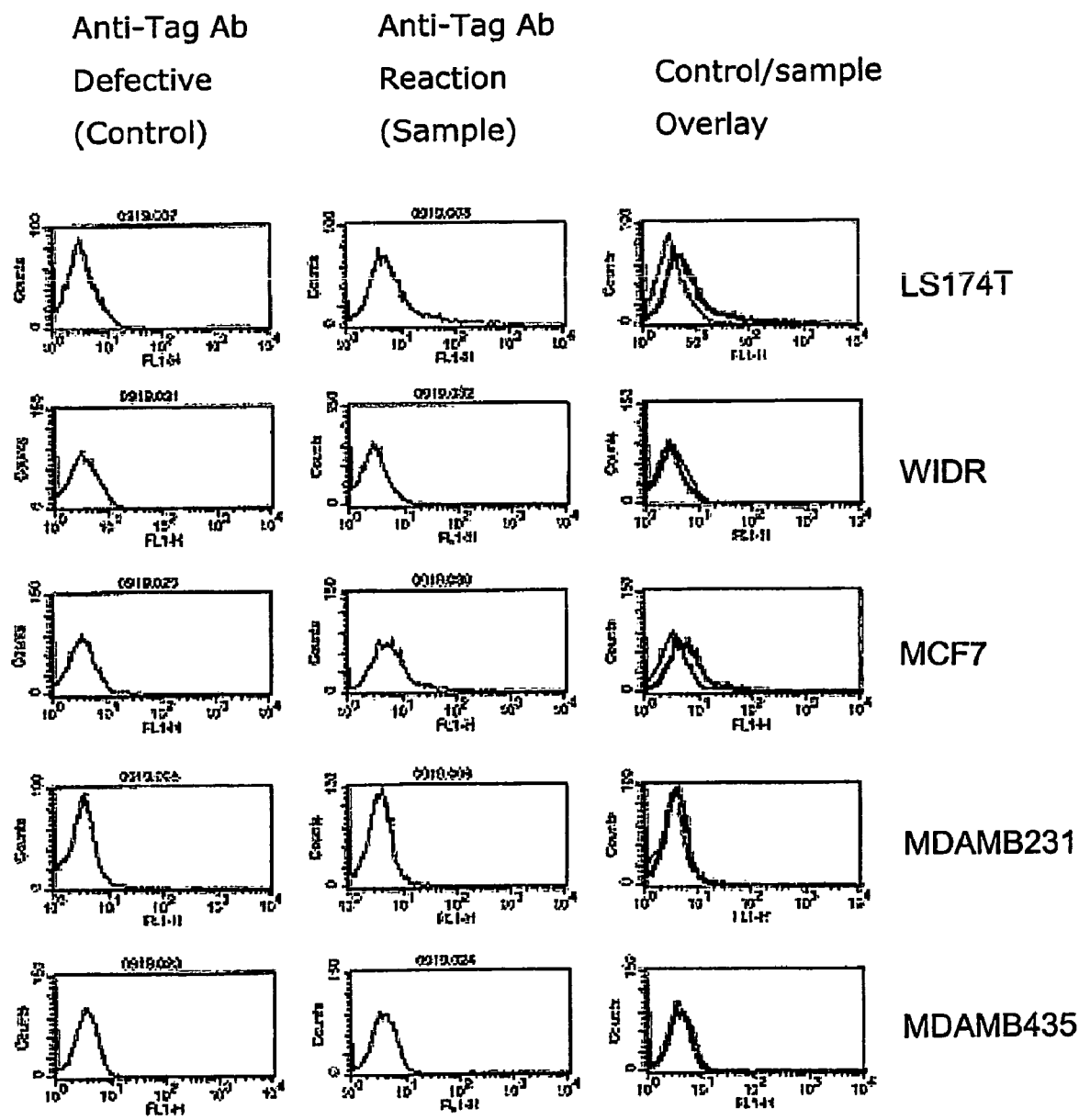
Figure 7B:
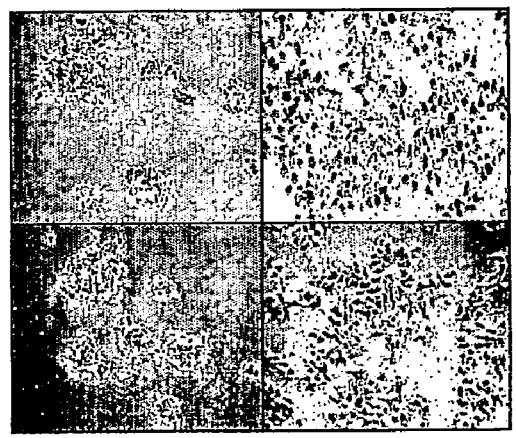
Figure 7B:
Figure 7B:

GP293 cells (Clontech, USA) expressing Gag-Pol proteins of moloney murine leukemia virus (Mo-MuLV) were employed for the production of retrovirus. GP293 cells were cultured in DMEM supplemented with 10% PBS (HyClone), 100 U/ml of penicillin G and 0.1 mg/ml of streptomycin, in a 5% $CO_2$ incubator at 37° C. The cultured GP293 cells were transduced with the recombinant retroviral vector pHEFv-GEL199 expressing the inventive fusion chimeric ligand together with the recombinant retroviral vector pMFG/LacZ/puro expressing β-galactosidase gene under the control of LTR promoter and containing a packaging signal (Oh et al., Mol. Cells 11: 192-197, 2001), according to the lipofectamine method (Invitrogen, USA). After 4 hrs, the cells were transferred into a fresh DMEM supplemented with 2% FBS, and further cultured at 37° C. for 2 days to obtain a culture solution containing cells and virus. The culture solution was passed through a filter having a pore size of 0.45 µm to remove cell debris, to obtain a cell-free virus culture solution. To confirm the virus production, the cell-free virus culture solution was subjected to centrifugation (Beckman sw55 rotor) at 8,000 rpm, 4° C. for 12 hrs to remove the supernatant, and then, the residual viral pellet was recovered. The viral pellet was suspended in a SDS-PAGE sample buffer solution and subjected to electrophoresis and western blot analyses to examine the expression of chimeric ligand (FIG. 6). SDS-PAGE and western blot analyses were carried out according to the same methods described in Example <1-3>. At this time, a mouse monoclonal antibody anti-PreS 1 and goat IgG anti-mouse IgG were employed as the primary and secondary antibodies, respectively.

As a result, the inventive fusion chimeric ligand FvGEL199 showed a band caused by antigen-antibody immune reaction at a position corresponding to a peptide having a molecular weight of 718 amino acids wherein the signal peptide and ™ regions were deleted (Lane 2 of FIG. 6). From these results, it was found that the recombinant retrovirus containing the inventive ScFv-GaLV Env GP fusion chimeric ligand is produced.

EXAMPLE 3

Target Cell Specific Infection of Retrovirus Expressing the ScFv-GaLV Env GP Chimeric Ligand <3-1> Confirmation of Tag-72 Surface Antigen Expressing Cancer Cell Lines To construct a mouse metastasis model using Tag-72 surface antigen-associated cell lines, the expression of Tag-72 surface antigen in several human cancer cell lines was examined by fluorescence-activated cell sorting (FACS) and immunohistochemical analyses.

First, human colon cancer cell lines LS174T (ATCC No. CL-188) and WiDr (ATCC No. CCL-218), human breast cancer cell lines MCF7 (KCLB No. 30022), MDA-MB231 (ATCC HTB-26) and MDA-MB435 (ATCC HTB-129) were subjected to the FACS analysis. Anti Tag-72 monoclonal antibody CC49 was employed as a primary antibody for examining the expression of Tag-72 surface antigen in several human cancer cell lines (Lee et al., Mol. Immunol. 36: 61-71, 1999). Each cancer cell line ($10^6$ cell/ml) was reacted with the anti Tag-72 primary antibody at 4° C. for 30 min. The cells were washed three times with a cold PBA solution and reacted with the anti-mouse IgG secondary antibody conjugated with a FITC (Jackson Immuno Research, USA) at 4° C. for 30 min. Then, the cells were washed three times with a cold PBA solution and subjected to the Facscan analysis (A of FIG. 7). As a result, while human colon cancer cell line LS174T and human breast cancer cell line MCF7 showed positive signals for the Tag-72 surface antigen, human breast cancer cell line MDA-MB231, human colon cancer cell lines WiDr and MDA-MB435, negative signals for the Tag-72 surface antigen.

Further, the expression of Tag-72 surface antigen by an immunohistochemical analysis was examined. The immunohistochemical analysis was carried out using system DAKO LSAB2 and alkaine phosphatase (#K674). Anti Tag-72 antibody AKA (KOREA PATENT NO: 318761) diluted with PBS in a ratio of 1:1,000 was employed as a primary antibody. The anti Tag-72 antibody was prepared by purifying the culture supernatant of chinese hamster ovary (CHO; Korea Patent Laid-Open Publication NO: 2003-13633) cells which express a humanized mouse monoclonal antibody against the Tag-72 surface antigen in a stable fashion, using a Hytrap Protein A column (Amersham, USA). A biotin-goat polyclonal antibody against human IgG H&L (ab6857-1, Aabcam) was diluted with PBS in a ratio of 1:1,000 and used as a secondary antibody. Further, a lavamisole solution (endogeous alkaline phosphatase inhibitor, X3021) was employed to prevent background staining.

As a result, while 10 to 20% or less of cells were stained in the breast cancer cell line MCF-7, 80 to 90% or more of cells of colon cancer cell line LS174T were stained, which means that the Tag-72 surface antigen was distributed on the cell surface. From these results, it was found that the colon cancer cell line LS174T and breast cancer cell line MCF-7 are Tag- 72 positive cell lines, and the colon cancer cell line WiDr and breast cancer cell lines MDA-MB435 and MDA-MB231 are Tag-72 negative cell lines (13 of FIG. 7).

<3-2>Confirmation of Target Cell Specific Infection

Tag-72 surface antigen positive or negative human cancer cell lines examined in Example <2-2-1> were infected with the recombinant retrovirus expressing the ScFv-GaLV Env GP chimeric ligand and the LacZ. After two days, the expression of LacZ gene was examined to confirm the target cell specific infection of the recombinant retrovirus.

In particular, packaging cell line GP293 cells were distributed on a 6-well plate at a concentration of $3 \times 10^5$ cells/well one day before the transduction. 0.5 μg each of expression vectors pHEGEL (wild-type GaLV Env GP) and pHEFv-GEL199 (ScFv-GaLV Env GP chimeric ligand) were mixed with 0.5 μg of pMFG/LacZ/puro transfer vector, respectively, and transduced into to the cells distributed at the well plate using a lipofectamine plus (Invitrogen, USA). The well plate was incubated in a mammalian cell incubator for 2 days under the condition of 37° C., 5% $CO_2$ to obtain a culture supernatant containing retrovirus. 293, LS174T, MCF-7, MDA-MB231 and MKN-75, target cells, were distributed on a 12-well plate at a concentration of $5 \times 10^4$ cells/well and left as it is for 24 hrs. The target cells were infected with each virus supernatant prepared above using a polybrene (Sigma) at a concentration of 8 μg/ml/well. 4 hrs after the infection, the infected cells were transferred in a fresh medium and further cultured for 48 hrs in a 37° C., 5% $CO_2$ incubator. When the cultivation was completed, the culture solution was removed, and the cell pellet was fixed with a cell fixing solution (1% formaldehyde, 0.2% glutaraldehyde) and kept at room temperature for 10 min to fix it. The suspension was washed three times with a PBS solution and subjected to X-gal staining (PBS, 0.2 M potassium ferrocyanide, 0.2 M potassium ferricyanide, 2.0 M $MgCl_2$ and 40 mg/ml X-gal) at 37° C. overnight to examine the presence of LacZ gene expression.

TABLE 2

| Target cell | Retroviral vector | |
| --- | --- | --- |
| | Wild-type | ScFv-GaLV Env GP |
| 293 | $2 \times 10^6$ | 36 |
| LS174T | $6 \times 10^3$ | 17 |
| MCF-7 | $5 \times 10^4$ | 121 |
| MDA-MB435 | $9 \times 10^4$ | 0 |
| MDA-MB231 | $1.5 \times 10^5$ | 0 |

Figure 8:
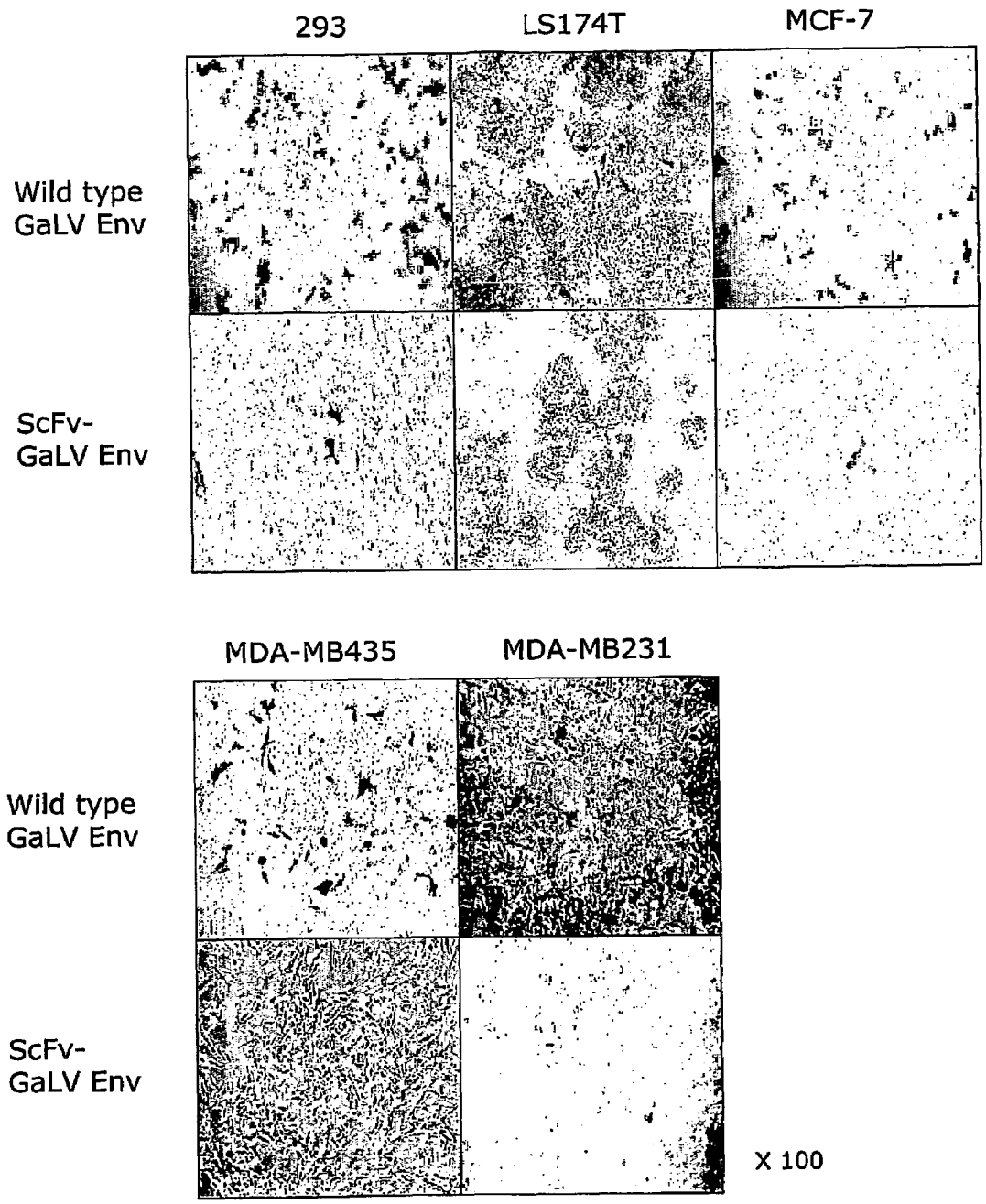

As shown in Table 2 and FIG. 8, the results of LacZ gene transduction using the wild-type GaLV Env GP expression vector pHEGEL showed that the transduction efficiency of 293 cell line was $2 \times 10^6$; those of cancer cell lines MDA-MB435, MDA-MB231 and MCF-7, ranging from 0.5 to $1.5 \times 10^5$; and that of LS174T cell line, $6 \times 10^3$. As a result of the LacZ gene transduction using the recombinant retroviral vector pHEFvGEL199 expressing the ScFv-GaLV Env GP chimeric ligand, it was found that while the LacZ gene was expressed in Tag-72 positive cell lines MCF-7 and LS174T together with 293 cell line, Tag-72 negative cell lines MDA-MB435 and MDA-MB231 do not express the LacZ gene. In particular, although there was no report that 293 cell line is Tag-72 positive, the reason why 293 cell line was infected with the inventive ScFv-GaLV Env GP chimeric ligand is because of non-specific infection due to its significantly higher infection efficiency than others. From these results, it was found that the recombinant vector pHEFvGEL199 expressing the inventive ScFv-GaLV Env GP chimeric ligand specifically binds to Tag-72 antigen expressing cells and efficiently delivers the LacZ gene (β-galactosidase) to target cells.

It has been reported that chimeric ligands show a lower viral titer than wild-type Env in other retroviral vectors including MLV. For example, while ecotropic Env or amphotropic Env shows a viral titer ranging from $10^5$ to $10^7$ according to the kind of target cells, most ScFv-Env GP chimeric ligands show less than a viral titer of $10^3$ even though there are some difference according to the target cell receptor, and accordingly, the viral titer of ScFv-Env GP chimeric ligands is lower by a factor of $10^2$ to $10^4$ than that of the wild-type Env (Chris A. Benedict. et al., *Human Gene Therapy* 10: 545-557, 1999; Mariana Marin. et al., *Journal of Virology* 70: 2957-2962, 1996; Te-Hua Tearina C. H. and Ralph Domburg, *Journal of Virology* 71: 720-725, 1997). This phenomenon is due to the reason that the original structure of the retrovirus is modified by an inserted foreign ligand into its envelope glycoprotein, which leads to the reduction of viral infectiousness. Generally, when a surface subunit (SU) of the envelope glycoprotien recognizes a specific receptor and binds to it, a conformational change is induced in the transmembrane (™) region capable of fusing, and then, virus infects target cells. At this time, the insertion of a foreign ligand induces a modification of the original structure and destroys the signal transfer from SU to TM, which in turn cannot cause the conformational change. As a result, although virus binds to a target cell and enters into the cell interior, membrane fusion does not occur, and accordingly, viral particles are not be introduced into the cytoplasm, which is the result of postbinding block and a major cause for the reduction of infectiousness. From the results stated above, it was found that the inventive ScFv-GaLV Env GP chimeric ligand FvGEL199 is capable of specifically infecting target cells at a higher transduction efficiency than any other retroviral vector reported before, and accordingly, effectively delivering a therapeutic gene to target cells.

EXAMPLE 4

Figure 9:
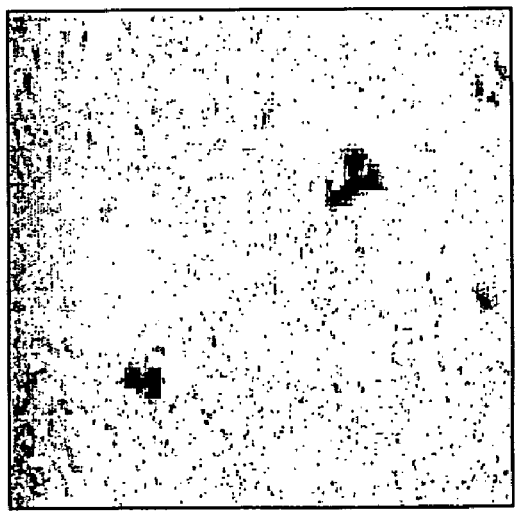
Figure 9:
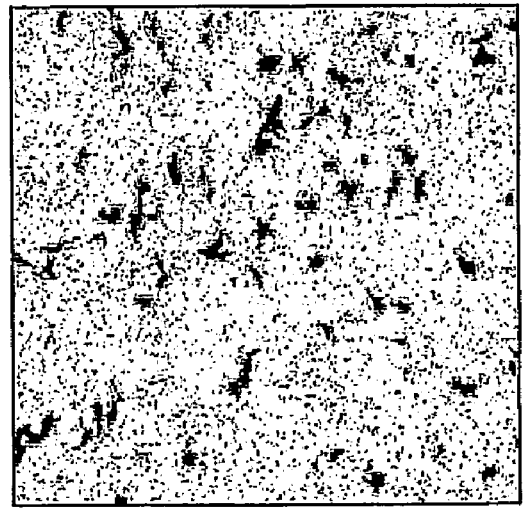

Preparation of Cancer Cell Targeting Packaging Cell Lines Expressing the ScFv-GaLV Env GP Chimeric Ligand Packaging cell line GP293 cells expressing Gag-Pol proteins were transfected with the recombinant vector pHEFv-GEL199 expressing the inventive ScFv-GaLV Env GP chimeric ligand using a lipofectamine plus (Invitrogen, USA). The transfected cells were treated with 400 μg/ml of G418 (neomycine) for 14 days to select 10 colonies and each colony was proliferated in an appropriate medium. The selected colony was transduced with 1 μg of retroviral transfer vector pMFG/LacZ/puro expressing LacZ reporter gene (β-galactosidase) (Oh et al., *Mol. Cells* 11: 192-197, 2001) and each virus was harvested 48 hrs after the transduction. Tag-72 positive cell line MCF-7 (KCLB 30022) was infected with each virus and the viral transduction efficiency was confirmed by examining the LacZ gene expression. The colony producing virus which shows the highest transduction efficiency was selected therefrom, and designated packaging cell line GP293HEFvGEL199 which continuously expresses the inventive ScFv-GaLV Env GP chimeric ligand. Further, vector pHEGEL expressing a wild-type GaLV Env was also transduced into target cells and the transduced colony was selected according to the same method described above, to obtain packaging cell line GP293HEGEL expressing the wild-type GaLV Env. FIG. 9 shows the results of infecting each target cell with virus which is obtained by transducing GP293HEFvGEL199 or GP293HEGEL packaging cell line prepared above with LacZ gene expressing retroviral transfer vector.

EXAMPLE 5

Figure 10:
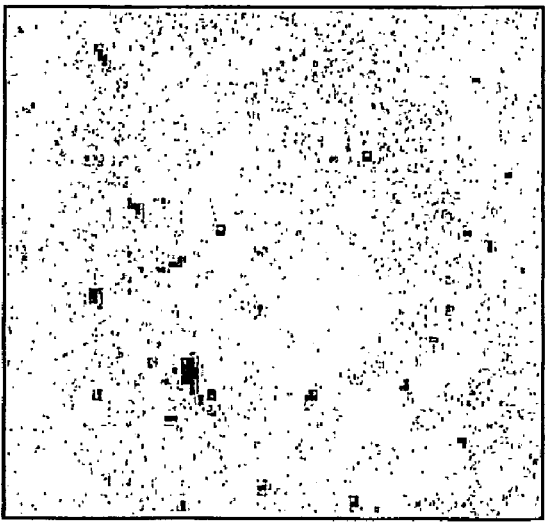
Figure 10:
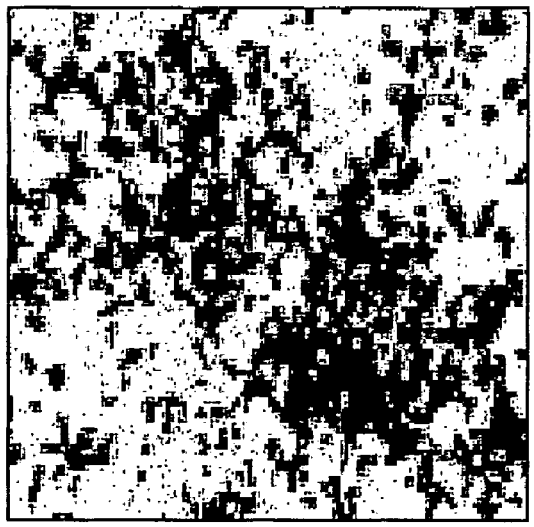

Preparation of Cancer Cell Targeting Retrovirus Producing Cell Lines Expressing the ScFv-GaLV Env GP Chimeric Ligand Packaging cell line GP293 cells ($3'10^5$ cells/6 wells) were transduced with the recombinant vector pHEFvGEL199 expressing the inventive ScFv-GaLV Env GP chimeric ligand together with retroviral transfer vector pMFG/LacZ/puro (0.5 μg) using a lipofectamine plus (Invitrogen, USA). The transduced cells were successively treated with 400 μg/ml of G418 (neomycine) and 0.5 μg/ml of puromicin for 2 weeks and 8 colonies were selected therefrom. The selected colonies were propagated in an appropriate medium to obtain a virus containing culture solution, and MCF-7 cells were infected with the resulting culture solution. As a result, the colony showing the highest viral titer was selected and cultivated, to obtain a virus producing cell line GP293HEFvGEL199/lacZ which is capable of continuously producing a LacZ gene expression retrovirus, the inventive ScFv-GaLV Env chimeric ligands being distributed on its outer membrane. Further, vector pHEGEL expressing a wild-type GaLV Env was also transduced into target cells and the transduced colony was selected according to the same method described above, to obtain virus producing cell line GP293HEGEL/lacZ which is capable of continuously producing the LacZ gene expression retrovirus having the wild-type GaLV Env. FIG. 10 shows the results of infecting each target cell with virus obtained by transducing GP293HEFvGEL199/lacZ and GP293HEGEL/lacZ virus producing cell lines prepared above, respectively.

EXAMPLE 6

Construction of Mouse Metastasis Model Using Tag-72 Antigen Associated Cell Lines As a result of examining the expression of Tag-72 surface antigen in various human cancer cell lines using FACS and immunohistochemical analyses in Example <3-1>, it was found that human breast cancer cell line MCF-7 and colon cancer cell line LS 174T are Tag-72 positive and human breast cancer cell lines MDA-MB231, MDA-MB435 and colon cancer cell line WIDR are Tag-72 negative. Since MDA-MB435 cell line shows relatively higher metastasis in the lung than MDA-MB231 cell line among Tag-72 negative cell lines (Lee & Welch, *Cancer Research* 57: 2384, 1997), MDA-MB435 cell line was employed for the construction of a cancer metastasis model. Further, MCF-7 breast cancer cell line (Tag-72 positive) is not employable for in vivo experiments because lung metastasis almost never occurs in them, but liver metastasis by an intraplenic injection and lung metastasis by an intravenous injection are possible in LS174T colon cancer cell line. Therefore, LS174T cell line was employed together with MDA-MB435 cell line for the construction of a cancer metastasis animal model.

Figure 11A:
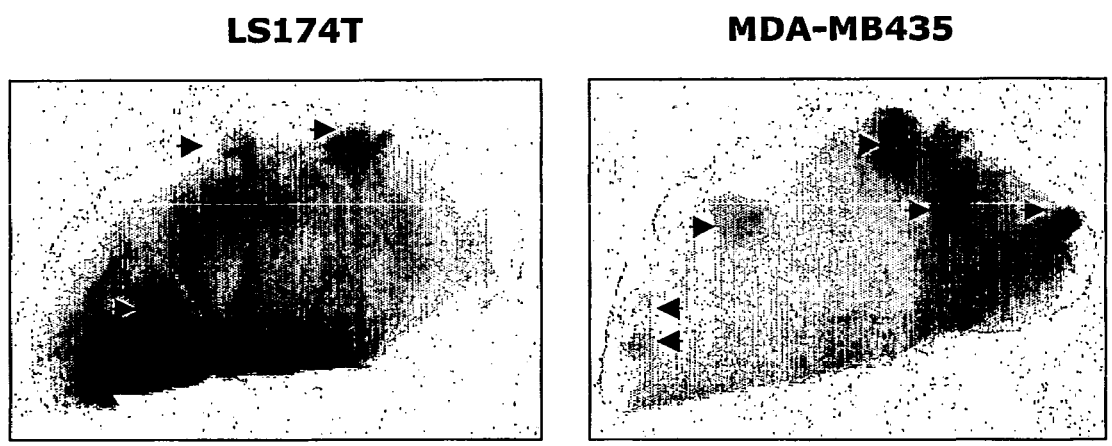
Figure 11B:
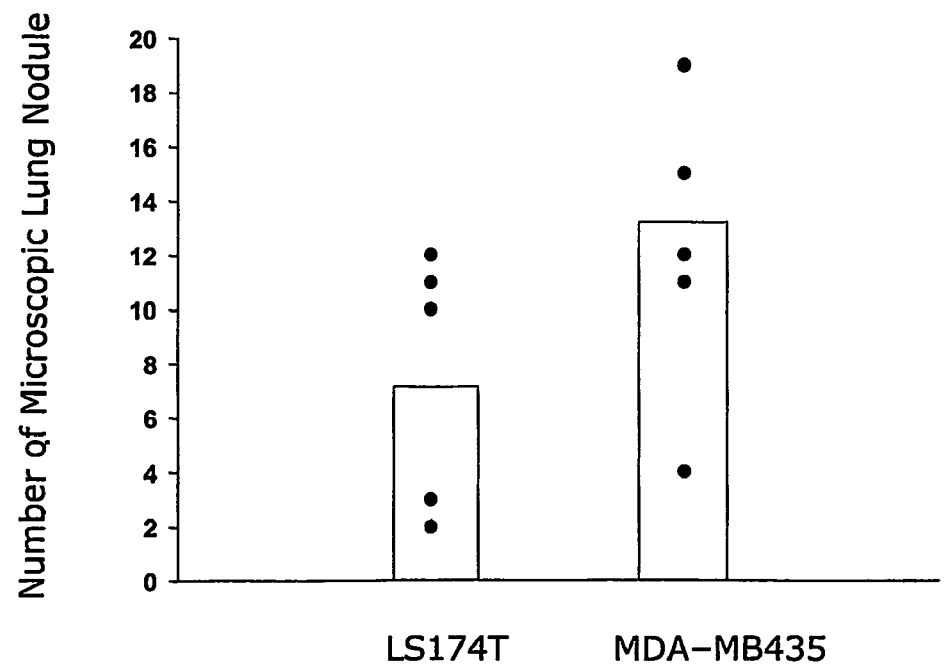

<6-1> Construction of Colon Cancer Metastasis Model Using an Intravenous Injection Method After the cultivation of Tag-72 positive LS 174T colon cancer cell line and Tag-72 negative MDA-MB435 breast cancer cell line, the cells were treated with trypsin-EDTA, harvested by centrifugation and washed twice with a serum free medium. The cells were washed twice with a PBS solution and injected into the tail vein of a 6-week old of female Balb/c nude mouse at a concentration of $1\times10^6$ cells/100 μl in PBS. After observing the mouse's condition for 6 weeks, the lung was extracted from the mouse and fixed in a 4% formalin solution to examine the number of lung nodules. As a result of examining lung metastsasis ability via an intravenous injection, it was found that 7.6 nodules were formed in LS174T colon cancer cell line and 12.2 nodules, in MDA-MB435 breast cancer cell line, on the average (FIG. 11*a* and 11*b*). Consequently, the lung metastasis model of human colon cancer cell line LS174T was employed as an animal model for testing the effectiveness of Tag-72 antigen specific cancer cell targeting gene therapeutic agent.

<6-2> Examination of in vivo Transduction Efficiency Using the Recombinant Retrovirus Vector Expressing the ScFv-GaLV Env GP Chimeric Ligand Packaging cell line GP293 cells were distributed on a 6-well plate at a concentration of $3\times10^5$ cells/well, the well plate was kept for 24 hrs, and then, the cells were transduced with retroviral vector pHEFvGEL199 expressing the ScFv-GaLV Env GP chimeric ligand together with retroviral transfer vector pMFG/LacZ/puro expressing P-galactosidase using a lipofectamine plus. The well plate was incubated in an animal cell incubator under the condition of 37° C., 5% $CO_2$ for 2 days, to obtain a virus producing cell line. Immediately after the cultured LS174T cells ($1\times10^6$ cells/50 μl in PBS) and MDA-MB435 cells ($1\times10^6$ cells/50 μl in PBS) were injected into the tail vein of each of 6-week old female Balb/c nude mice at a concentration of $1\times10^6$ cells/100 μl in PBS, the virus producing cell line obtained above ($1\times10^6$ cells/50 μl in PBS) was injected to each mouse according to the same method described above. Then, the virus producing cell line ($1\times10^6$ cells/100 μl in PBS) was intravenously injected to each mouse for 6 weeks at an interval of 3 days. After 6 weeks, the mouse was sacrificed to extract the lung, and the lung was soaked in a fixing solution, and then, subjected to X-gal staining to examine in vivo transduction efficiency.

Figure 12A:
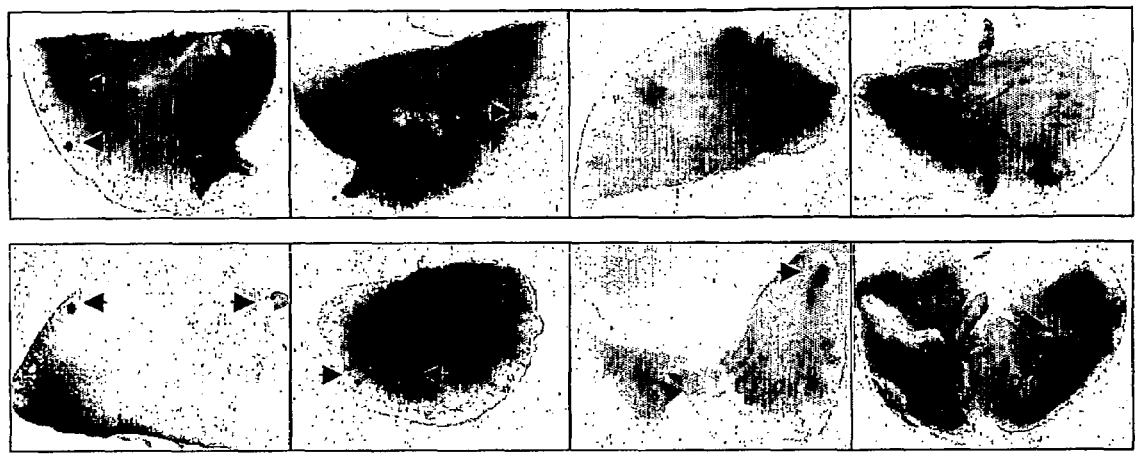
Figure 12B:
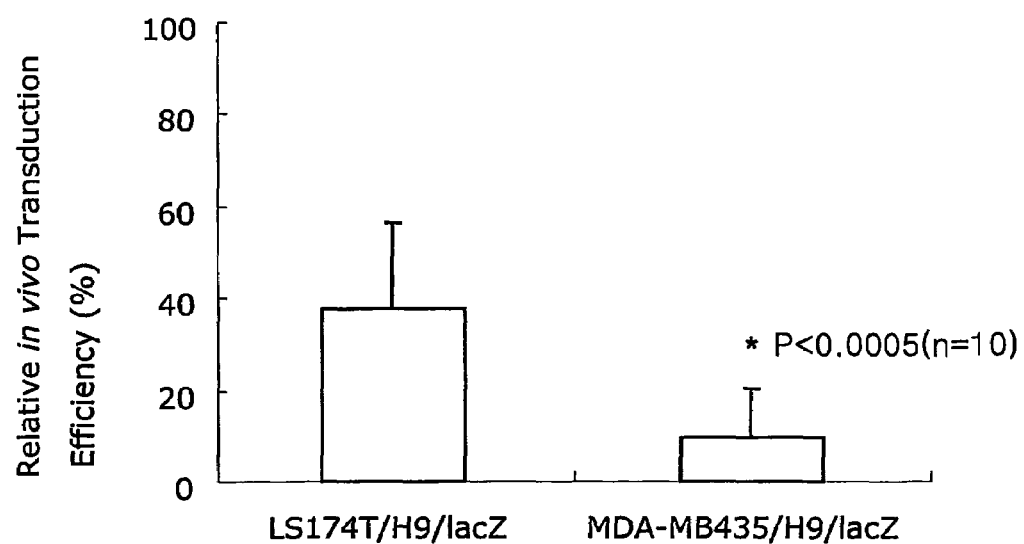

As a result, it was found that in case of forming lung nodules by the intravenous injection of Tag-72 positive cell line LS174T, the transduction of LacZ reporter gene mediated by the inventive ScFv-GaLV Env GP chimeric ligand was effective and Tag-72 specific, at efficiency of 37.8%. Meanwhile, only 9.77% of lung modules formed by the intravenous injection of Tag-72 negative cell line MDA-MB435 was stained. From these results, it was found that the cancer cell targeting gene delivery system using the inventive ScFv-GaLV Env GP chimeric ligand expression vector is very specific for Tag-72 surface antigen and efficiently transduced into target cells. FIG. 12*a* shows dissecting microscope pictures of lung modules stained by introducing and expressing the LacZ reporter gene (β-galactosidase) using the inventive ScFv-GaLV Env GP chimeric ligand FvGEL199 expression retroviral vector. Further, Table 3 represents the number of nodules found in the extracted lung and the number of stained nodules, and FIG. 12*b*, a graph depicting the results of Table 3 in percentages (%).

TABLE 3

| | LS174T/ScFv-Env/LacZ | | | MDA-MB435/ScFv-Env/LacZ | | |
|---|---|---|---|---|---|---|
| Mouse | Nodule | Dying | Transduction efficiency (%) | Nodule | Dying | Transduction efficiency (%) |
| 1 | 5 | 2 | 40 | 8 | 0 | 0 |
| 2 | 3 | 1 | 33 | 6 | 1 | 16.7 |
| 3 | 6 | 2 | 33 | 6 | 0 | 0 |
| 4 | 2 | 1 | 50 | 3 | 0 | 0 |
| 5 | 7 | 2 | 29 | 7 | 0 | 0 |
| 6 | 2 | 0 | 0 | 4 | 1 | 25 |
| 7 | 3 | 2 | 67 | 12 | 2 | 16.7 |
| 8 | 40 | 4 | 40 | 11 | 2 | 18.2 |
| 9 | 11 | 3 | 28 | 15 | 0 | 0 |
| 10 | 12 | 7 | 58 | 19 | 4 | 21.1 |
| Average | 6.1 | 2.4 | 37.8 | 9.1 | 1 | 9.77 |

While the embodiments of the subject invention have been described and illustrated, it is obvious that various changes and modifications can be made therein without departing from the spirit of the present invention which should be limited only by the scope of the appended claims.

What is claimed is:

1. A chimeric ligand protein in the form of a fusion polypeptide of a single-chain antibody (ScFv) specific for a surface antigen of tumor associated glycoprotein 72 (Tag-72) and gibbon ape leukemia virus (GaLV) envelope glycoprotein, wherein the ScFv is inserted between the 199$^{th}$ and 200$^{th}$ amino acid residues of a surface subunit of GaLV envelope glycoprotein.

2. The chimeric ligand protein of claim 1, which has the amino acid sequence of SEQ ID NO:9.

3. A gene encoding the chimeric ligand protein of claim 1.

4. The gene of claim 3, which has the nucleotide sequence of SEQ ID NO: 8.

5. A recombinant expression vector containing the gene of claim 3.

6. The recombinant expression vector of claim 5, which is pHEFvGEL199 (Accession No; KCTC-10596BP).

7. A packaging cell line transduced with the recombinant expression vector of claim 5.

8. A recombinant retrovirus produced by the packaging cell line of claim 7, wherein the chimeric ligand is distributed on its outer membrane.

* * * * *

SEQUENCE LISTING

<160> NUMBER OF SEQ ID NOS: 11

<210> SEQ ID NO 1
<211> LENGTH: 36
<212> TYPE: DNA
<213> ORGANISM: Artificial Sequence
<220> FEATURE:
<223> OTHER INFORMATION: Env F primer

<400> SEQUENCE: 1
cgcggatccg aattccatac ctggtgttgc tgacta        36

<210> SEQ ID NO 2
<211> LENGTH: 47
<212> TYPE: DNA
<213> ORGANISM: Artificial Sequence
<220> FEATURE:
<223> OTHER INFORMATION: 597LN primer

<400> SEQUENCE: 2
agctggacct ggctgccacc acctccgcta ttttggtccc attttac        47

<210> SEQ ID NO 3
<211> LENGTH: 49
<212> TYPE: DNA
<213> ORGANISM: Artificial Sequence
<220> FEATURE:
<223> OTHER INFORMATION: LC597 primer

<400> SEQUENCE: 3
caaccccgcc gcaggtggag gaggcagtga atggactcaa aaatttcaa        49

<210> SEQ ID NO 4
<211> LENGTH: 35
<212> TYPE: DNA
<213> ORGANISM: Artificial Sequence
<220> FEATURE:
<223> OTHER INFORMATION: Spike R2 primer

<400> SEQUENCE: 4
tgctctagaa ttcttaaagg ttaccttcgt tctct        35

<210> SEQ ID NO 5
<211> LENGTH: 36
<212> TYPE: DNA
<213> ORGANISM: Artificial Sequence
<220> FEATURE:

<223> OTHER INFORMATION: LnkNScFv primer

<400> SEQUENCE: 5
ggaggtggtg gcagccaggt ccagctagtg cagtct                          36

<210> SEQ ID NO 6
<211> LENGTH: 36
<212> TYPE: DNA
<213> ORGANISM: Artificial Sequence
<220> FEATURE:
<223> OTHER INFORMATION: ScFvLnkC primer

<400> SEQUENCE: 6
actgcctcct ccacctgcgg cggggttgaa gtccca                          36

<210> SEQ ID NO 7
<211> LENGTH: 2058
<212> TYPE: DNA
<213> ORGANISM: Gibbon Ape leukemia virus
<220> FEATURE:
<221> NAME/KEY: sig_peptide
<222> LOCATION: (1)..(126)
<220> FEATURE:
<221> NAME/KEY: misc_feature
<222> LOCATION: (127)..(1467)
<223> OTHER INFORMATION: surface subunit region
<220> FEATURE:
<221> NAME/KEY: misc_feature
<222> LOCATION: (1468)..(2025)
<223> OTHER INFORMATION: transmembrain domain

<400> SEQUENCE: 7

| | | |
|---|---|---|
| atggtattgc tgcctgggtc catgcttctc acctcaaacc tgcaccacct tcggcaccag | 60 |
| atgagtcctg ggagctggaa aagactgatc atcctcttaa gctgcgtatt cggcggcggc | 120 |
| gggacgagtc tgcaaaataa gaaccccac cagcccatga ccctcacttg caggtactg | 180 |
| tcccaaactg gagacgttgt ctgggataca aaggcagtcc agcccccttg acttggtgg | 240 |
| cccacactta aacctgatgt atgtgccttg gcggctagtc ttgagtcctg ggatatcccg | 300 |
| ggaaccgatg tctcgtcctc taaacgagtc agacctccgg actcagacta tactgccgct | 360 |
| tataagcaaa tcacctgggg agccataggg tgcagctacc ctcgggctag gactagaatg | 420 |
| gcaagctcta ccttctacgt atgtccccgg gatggccgga ccctttcaga gctagaagg | 480 |
| tgcgggggc tagaatccct atactgtaaa gaatgggatt gtgagaccac ggggaccggt | 540 |
| tattggctat ctaaatcctc aaaagaccct ataactgtaa aatgggacca aaatagcgaa | 600 |
| tggactcaaa aatttcaaca gtgtcaccag accggctggt gtaaccccct taaaatagat | 660 |
| ttcacagaca aaggaaaatt atccaaggac tggataacgg gaaaaacctg gggattaaga | 720 |
| ttctatgtgt ctggacatcc aggcgtacag ttcaccattc gcttaaaaat caccaacatg | 780 |
| ccagctgtgg cagtaggtcc tgacctcgtc cttgtggaac aaggacctcc tagaacgtcc | 840 |
| ctcgctctcc cacctcctct tccccccaagg gaagcgccac cgccatctct ccccgactct | 900 |
| aactccacag ccctggcgac tagtgcacaa actcccacgg tgagaaaaac aattgttacc | 960 |
| ctaaacactc cgcctccac cacaggcgac agacttttg atcttgtgca gggggccttc | 1020 |
| ctaaccttaa atgctaccaa cccaggggcc actgagtctt gctggctttg tttggccatg | 1080 |
| ggcccccctt attatgaagc aatagcctca tcaggagagg tcgcctactc caccgacctt | 1140 |
| gaccggtgcc gctgggggac ccaaggaaag ctcaccctca ctgaggtctc aggacacggg | 1200 |
| ttgtgcatag gaaaggtgcc ctttacccat cagcatctct gcaatcagac cctatccatc | 1260 |

```
aattcctccg gagaccatca gtatctgctc ccctccaacc atagctggtg ggcttgcagc    1320
actggcctca ccccttgcct ctccacctca gttttaatc agactagaga tttctgtatc    1380
caggtccagc tgattcctcg catctattac tatcctgaag aagttttgtt acaggcctat    1440
gacaattctc accccaggac taaaagagag gctgtctcac ttaccctagc tgttttactg    1500
gggttgggaa tcacggcggg aataggtact ggttcaactg ccttaattaa aggacctata    1560
gacctccagc aaggcctgac aagcctccag atcgccatag atgctgacct ccgggccctc    1620
caagactcag tcagcaagtt agaggactca ctgacttccc tgtccgaggt agtgctccaa    1680
aataggagag gccttgactt gctgtttcta aaagaaggtg gcctctgtgc ggccctaaag    1740
gaagagtgct gttttacat agaccactca ggtgcagtac gggactccat gaaaaaactc    1800
aaagaaaaac tggataaaag acagttagag cgccagaaaa gccaaaactg gtatgaagga    1860
tggttcaata actcccttg gttcactacc ctgctatcaa ccatcgctgg gccctatta    1920 ctcctccttc tgttgctcat cctcgggcca tgcatcatca ataagttagt tcaattcatc    1980
aatgatagga taagtgcagt taaaattctg gtccttagac aaaaatatca ggccctagag    2040
aacgaaggta accttaa                                                   2058

<210> SEQ ID NO 8
<211> LENGTH: 786
<212> TYPE: DNA
<213> ORGANISM: Artificial sequence
<220> FEATURE:
<223> OTHER INFORMATION: Single-chain antibody Tag-72pS1 specific for
      Tag-72 surface antigen
<220> FEATURE:
<221> NAME/KEY: misc_feature
<222> LOCATION: (1)..(345)
<223> OTHER INFORMATION: heavy chain (H) variable region
<220> FEATURE:
<221> NAME/KEY: misc_feature
<222> LOCATION: (346)..(390)
<223> OTHER INFORMATION: (Gly4Ser)3 linker
<220> FEATURE:
<221> NAME/KEY: misc_feature
<222> LOCATION: (391)..(738)
<223> OTHER INFORMATION: light chain (L) variable region
<220> FEATURE:
<221> NAME/KEY: misc_feature
<222> LOCATION: (739)..(777)
<223> OTHER INFORMATION: PreS1 Tag
<220> FEATURE:
<221> NAME/KEY: misc_feature
<222> LOCATION: (778)..(786)
<223> OTHER INFORMATION: C-terminal extra termination sequence

<400> SEQUENCE: 8
caggtccagc tagtgcagtc tggggctgaa gtgaagaagc tggggcttc agtgaaggtg      60 tcctgcaagg cttctggcta caccttcact gaccatgcaa ttcactgggt gcgccaggcc    120
cctggacaac gccttgagtg gatgggatat tttctcctg caacgatga ttttaaatac     180 tcccagaagt tccagggacg cgtgacaatc actgcagaca atccgcgag cacagcctac    240 atggagctga gcagcctgag atctgaggac acggcggtct attactgtgc aagatcgttg    300
aacatggcat actggggcca aggactctg gtcactgtct cttcaggtgg aggcggttca    360
ggcggaggtg gctctggcgg tggcggatcg gacattgtga tgacccagtc tccagactcc    420
ctggctgtgt ctctgggcga gagggccacc atcaactgca agtccagcca gagtgtttta    480
tacagcagca caataagaa ctacttagct tggtaccagc agaaaccagg acagcctcct    540
aagctgctca tttactgggc atctacccgg gaatccgggg tccctgaccg attcagtggc    600
```

-continued

| | |
|---|---|
| agcgggtctg ggacagattt cactctcacc atcagcagcc tgcaggctga agatgtggca | 660 |
| gtttattact gtcagcaata ttattcctat ccgttgacgt tcggccaagg gaccaaggtg | 720 |
| gaaatcaaag cggccgcagg agccaacgca acaatccag attgggactt caaccccgcc | 780 |
| gcatag | 786 |

<210> SEQ ID NO 9
<211> LENGTH: 13
<212> TYPE: PRT
<213> ORGANISM: Artificial sequence
<220> FEATURE:
<223> OTHER INFORMATION: PreS1 epitope

<400> SEQUENCE: 9

Gly Ala Asn Ala Asn Asn Pro Asp Trp Asp Phe Asn Pro
 1               5                  10

<210> SEQ ID NO 10
<211> LENGTH: 2871
<212> TYPE: DNA
<213> ORGANISM: Artificial Sequence
<220> FEATURE:
<223> OTHER INFORMATION: ScFv-GaLV Env GP chimeric peptide (FvGEL199)
      DNA

<400> SEQUENCE: 10

| | |
|---|---|
| atggtattgc tgcctgggtc catgcttctc acctcaaacc tgcaccacct tcggcaccag | 60 |
| atgagtcctg ggagctggaa aagactgatc atcctcttaa gctgcgtatt cggcggcggc | 120 |
| gggacgagtc tgcaaaataa gaaccccac cagcccatga ccctcacttg gcaggtactg | 180 |
| tcccaaactg gagacgttgt ctgggataca aaggcagtcc agcccccttg gacttggtgg | 240 |
| cccacactta aacctgatgt atgtgccttg gcggctagtc ttgagtcctg ggatatcccg | 300 |
| ggaaccgatg tctcgtcctc taaacgagtc agacctccgg actcagacta tactgccgct | 360 |
| tataagcaaa tcacctgggg agccataggg tgcagctacc ctcgggctag gactagaatg | 420 |
| gcaagctcta ccttctacgt atgtcccgg gatggccgga ccctttcaga agctagaagg | 480 |
| tgcggggggc tagaatccct atactgtaaa gaatgggatt gtgagaccac ggggaccggt | 540 |
| tattggctat ctaaatcctc aaaagacctc ataactgtaa aatgggacca aatagcgga | 600 |
| ggtggtggca gccaggtcca gctagtgcag tctggggctg aagtgaagaa gcctggggct | 660 |
| tcagtgaagg tgtcctgcaa ggcttctggc tacaccttca ctgaccatgc aattcactgg | 720 |
| gtgcgccagg cccctggaca acgccttgag tggatgggat atttttctcc tggcaacgat | 780 |
| gattttaaat actcccagaa gttccaggga cgcgtgacaa tcactgcaga caaatccgcg | 840 |
| agcacagcct acatggagct gagcagcctg agatctgagg acacggcggt ctattactgt | 900 |
| gcaagatcgt tgaacatggc atactggggc caagggactc tggtcactgt ctcttcaggt | 960 |
| ggaggcggtt caggcggagg tggctctggc ggtggcggat cggacattgt gatgacccag | 1020 |
| tctccagact ccctggctgt gtctctgggc gagagggcca ccatcaactg caagtccagc | 1080 |
| cagagtgttt tatacagcag caacaataag aactacttag cttggtacca gcagaaacca | 1140 |
| ggacagcctc ctaagctgct catttactgg gcatctaccc gggaatccgg ggtccctgac | 1200 |
| cgattcagtg gcagcgggtc tgggacagat ttcactctca ccatcagcag cctgcaggct | 1260 |
| gaagatgtgg cagtttatta ctgtcagcaa tattattcct atccgttgac gttcggccaa | 1320 |
| gggaccaagg tggaaatcaa agcggccgca ggagccaacg caacaatcc agattgggac | 1380 |
| ttcaaccccg ccgcaggtgg aggaggcagt gaatggactc aaaaatttca acagtgtcac | 1440 |

-continued

```
cagaccggct ggtgtaaccc ccttaaaata gatttcacag acaaaggaaa attatccaag     1500
gactggataa cgggaaaaac ctggggatta agattctatg tgtctggaca tccaggcgta     1560
cagttcacca ttcgcttaaa aatcaccaac atgccagctg tggcagtagg tcctgacctc     1620
gtccttgtgg aacaaggacc tcctagaacg tccctcgctc tcccacctcc tcttccccca     1680
agggaagcgc caccgccatc tctccccgac tctaactcca cagccctggc gactagtgca     1740
caaactccca cggtgagaaa acaattgtt  accctaaaca ctccgcctcc caccacaggc     1800
gacagacttt tgatcttgt  gcaggggggcc ttcctaacct aaatgctac  caacccaggg     1860 gccactgagt cttgctggct ttgtttggcc atgggccccc cttattatga agcaatagcc     1920
tcatcaggag aggtcgccta ctccaccgac cttgaccggt gccgctgggg acccaagga     1980 aagctcaccc tcactgaggt ctcaggacac gggttgtgca taggaaaggt gcccttacc     2040 catcagcatc tctgcaatca gaccctatcc atcaattcct ccggagacca tcagtatctg     2100
ctcccctcca accatagctg gtgggcttgc agcactggcc tcacccettg cctctccacc     2160 tcagttttta atcagactag agatttctgt atccaggtcc agctgattcc tcgcatctat     2220
tactatcctg aagaagtttt gttacaggcc tatgacaatt ctcaccccag gactaaaaga     2280
gaggctgtct cacttaccct agctgtttta ctggggttgg gaatcacggc gggaataggt     2340
actggttcaa ctgccttaat taaaggacct ataggacctcc agcaaggcct gacaagcctc     2400
cagatcgcca tagatgctga cctccgggcc ctccaagact cagtcagcaa gttagaggac     2460
tcactgactt ccctgtccga ggtagtgctc caaatagga gaggcttga cttgctgttt     2520 ctaaaagaag gtggcctctg tgcggccta aaggaagagt gctgttttta catagaccac     2580
tcaggtgcag tacgggactc catgaaaaaa ctcaaagaaa aactggataa aagacagtta     2640
gagcgccaga aaagccaaaa ctggtatgaa ggatggttca ataactcccc ttggttcact     2700
accctgctat caaccatcgc tgggcccta ttactcctcc ttctgttgct catcctcggg     2760
ccatgcatca tcaataagtt agttcaattc atcaatgata ggataagtgc agttaaaatt     2820
ctggtcctta gacaaaaata tcaggcccta gagaacgaag gtaaccttta a              2871
```

<210> SEQ ID NO 11
<211> LENGTH: 956
<212> TYPE: PRT
<213> ORGANISM: Artificial Sequence
<220> FEATURE:
<223> OTHER INFORMATION: ScFv-GaLV Env GP chimeric ligand (FvGEL199)

<400> SEQUENCE: 11

```
Met Val Leu Leu Pro Gly Ser Met Leu Leu Thr Ser Asn Leu His His
  1               5                  10                  15

Leu Arg His Gln Met Ser Pro Gly Ser Trp Lys Arg Leu Ile Ile Leu
                 20                  25                  30

Leu Ser Cys Val Phe Gly Gly Gly Gly Thr Ser Leu Gln Asn Lys Asn
             35                  40                  45

Pro His Gln Pro Met Thr Leu Thr Trp Gln Val Leu Ser Gln Thr Gly
         50                  55                  60

Asp Val Val Trp Asp Thr Lys Ala Val Gln Pro Pro Trp Thr Trp Trp
     65                  70                  75                  80

Pro Thr Leu Lys Pro Asp Val Cys Ala Leu Ala Ala Ser Leu Glu Ser
                 85                  90                  95

Trp Asp Ile Pro Gly Thr Asp Val Ser Ser Ser Lys Arg Val Arg Pro
                100                 105                 110
```

```
Pro Asp Ser Asp Tyr Thr Ala Ala Tyr Lys Gln Ile Thr Trp Gly Ala
        115                 120                 125
Ile Gly Cys Ser Tyr Pro Arg Ala Arg Thr Arg Met Ala Ser Ser Thr
    130                 135                 140
Phe Tyr Val Cys Pro Arg Asp Gly Arg Thr Leu Ser Glu Ala Arg Arg
145                 150                 155                 160
Cys Gly Gly Leu Glu Ser Leu Tyr Cys Lys Glu Trp Asp Cys Glu Thr
                165                 170                 175
Thr Gly Thr Gly Tyr Trp Leu Ser Lys Ser Lys Asp Leu Ile Thr
            180                 185                 190
Val Lys Trp Asp Gln Asn Ser Gly Gly Gly Ser Gln Val Gln Leu
    195                 200                 205
Val Gln Ser Gly Ala Glu Val Lys Lys Pro Gly Ala Ser Val Lys Val
    210                 215                 220
Ser Cys Lys Ala Ser Gly Tyr Thr Phe Thr Asp His Ala Ile His Trp
225                 230                 235                 240
Val Arg Gln Ala Pro Gly Gln Arg Leu Glu Trp Met Gly Tyr Phe Ser
                245                 250                 255
Pro Gly Asn Asp Asp Phe Lys Tyr Ser Gln Lys Phe Gln Gly Arg Val
                260                 265                 270
Thr Ile Thr Ala Asp Lys Ser Ala Ser Thr Ala Tyr Met Glu Leu Ser
            275                 280                 285
Ser Leu Arg Ser Glu Asp Thr Ala Val Tyr Tyr Cys Ala Arg Ser Leu
    290                 295                 300
Asp Met Ala Tyr Trp Gly Gln Gly Thr Leu Val Thr Val Ser Ser Gly
305                 310                 315                 320
Gly Gly Gly Ser Gly Gly Gly Ser Gly Gly Gly Ser Asp Ile
                325                 330                 335
Val Met Thr Gln Ser Pro Asp Ser Leu Ala Val Ser Leu Gly Glu Arg
            340                 345                 350
Ala Thr Ile Asn Cys Lys Ser Ser Gln Ser Val Leu Tyr Ser Ser Asn
    355                 360                 365
Asn Lys Asn Tyr Leu Ala Trp Tyr Gln Gln Lys Pro Gly Gln Pro Pro
    370                 375                 380
Lys Leu Leu Ile Tyr Trp Ala Ser Thr Arg Glu Ser Gly Val Pro Asp
385                 390                 395                 400
Arg Phe Ser Gly Ser Gly Ser Gly Thr Asp Phe Thr Leu Thr Ile Ser
                405                 410                 415
Ser Leu Gln Ala Glu Asp Val Ala Val Tyr Tyr Cys Gln Gln Tyr Tyr
            420                 425                 430
Ser Tyr Pro Leu Thr Phe Gly Gln Gly Thr Lys Val Glu Ile Lys Ala
    435                 440                 445
Ala Ala Gly Ala Asn Ala Asn Asn Pro Asp Trp Asp Phe Asn Pro Ala
    450                 455                 460
Ala Gly Gly Gly Ser Glu Trp Thr Gln Lys Phe Gln Gln Cys His
465                 470                 475                 480
Gln Thr Gly Trp Cys Asn Pro Leu Lys Ile Asp Phe Thr Asp Lys Gly
                485                 490                 495
Lys Leu Ser Lys Asp Trp Ile Thr Gly Lys Thr Trp Gly Leu Arg Phe
            500                 505                 510
Tyr Val Ser Gly His Pro Gly Val Gln Phe Thr Ile Arg Leu Lys Ile
    515                 520                 525
```

-continued

```
Thr Asn Met Pro Ala Val Ala Val Gly Pro Asp Leu Val Leu Val Glu
    530             535             540
Gln Gly Pro Pro Arg Thr Ser Leu Ala Leu Pro Pro Leu Pro Pro
545             550             555             560
Arg Glu Ala Pro Pro Ser Leu Pro Asp Ser Asn Ser Thr Ala Leu
                565             570             575
Ala Thr Ser Ala Gln Thr Pro Thr Val Arg Lys Thr Ile Val Thr Leu
            580             585             590
Asn Thr Pro Pro Thr Thr Gly Asp Arg Leu Phe Asp Leu Val Gln
        595             600             605
Gly Ala Phe Leu Thr Leu Asn Ala Thr Asn Pro Gly Ala Thr Glu Ser
    610             615             620
Cys Trp Leu Cys Leu Ala Met Gly Pro Pro Tyr Tyr Glu Ala Ile Ala
625             630             635             640
Ser Ser Gly Glu Val Ala Tyr Ser Thr Asp Leu Asp Arg Cys Arg Trp
                645             650             655
Gly Thr Gln Gly Lys Leu Thr Leu Thr Glu Val Ser Gly His Gly Leu
            660             665             670
Cys Ile Gly Lys Val Pro Phe Thr His Gln His Leu Cys Asn Gln Thr
        675             680             685
Leu Ser Ile Asn Ser Ser Gly Asp His Gln Tyr Leu Leu Pro Ser Asn
    690             695             700
His Ser Trp Trp Ala Cys Ser Thr Gly Leu Thr Pro Cys Leu Ser Thr
705             710             715             720
Ser Val Phe Asn Gln Thr Arg Asp Phe Cys Ile Gln Val Gln Leu Ile
                725             730             735
Pro Arg Ile Tyr Tyr Tyr Pro Glu Glu Val Leu Leu Gln Ala Tyr Asp
            740             745             750
Asn Ser His Pro Arg Thr Lys Arg Glu Ala Val Ser Leu Thr Leu Ala
        755             760             765
Val Leu Leu Gly Leu Gly Ile Thr Ala Gly Ile Gly Thr Gly Ser Thr
    770             775             780
Ala Leu Ile Lys Gly Pro Ile Asp Leu Gln Gln Gly Leu Thr Ser Leu
785             790             795             800
Gln Ile Ala Ile Asp Ala Asp Leu Arg Ala Leu Gln Asp Ser Val Ser
                805             810             815
Lys Leu Glu Asp Ser Leu Thr Ser Leu Ser Glu Val Val Leu Gln Asn
            820             825             830
Arg Arg Gly Leu Asp Leu Leu Phe Leu Lys Glu Gly Gly Leu Cys Ala
        835             840             845
Ala Leu Lys Glu Glu Cys Cys Phe Tyr Ile Asp His Ser Gly Ala Val
    850             855             860
Arg Asp Ser Met Lys Lys Leu Lys Glu Lys Leu Asp Lys Arg Gln Leu
865             870             875             880
Glu Arg Gln Lys Ser Gln Asn Trp Tyr Glu Gly Trp Phe Asn Asn Ser
                885             890             895
Pro Trp Phe Thr Thr Leu Leu Ser Thr Ile Ala Gly Pro Leu Leu Leu
            900             905             910
Leu Leu Leu Leu Leu Ile Leu Gly Pro Cys Ile Ile Asn Lys Leu Val
        915             920             925
```

```
Gln Phe Ile Asn Asp Arg Ile Ser Ala Val Lys Ile Leu Val Leu Arg
    930                 935                 940

Gln Lys Tyr Gln Ala Leu Glu Asn Glu Gly Asn Leu
945                 950                 955
```